(12) United States Patent
Podoleanu et al.

(10) Patent No.: US 7,535,577 B2
(45) Date of Patent: May 19, 2009

(54) OPTICAL MAPPING APPARATUS WITH OPTIMIZED OCT CONFIGURATION

(75) Inventors: Adrian Gh. Podoleanu, Canterbury (GB); David A. Jackson, Canterbury (GB); John A. Rogers, Canterbury (GB); George M. Dobre, London (GB); Radu G. Cucu, Canterbury (GB)

(73) Assignee: OTI Ophthalmic Technologies Inc. (CA)

( * ) Notice: Subject to any disclaimer, the term of this patent is extended or adjusted under 35 U.S.C. 154(b) by 37 days.

(21) Appl. No.: 11/828,764

(22) Filed: Jul. 26, 2007

(65) Prior Publication Data

US 2008/0013078 A1 Jan. 17, 2008

Related U.S. Application Data

(63) Continuation of application No. 11/561,682, filed on Nov. 20, 2006, now abandoned, and a continuation of application No. 11/177,047, filed on Jul. 8, 2005, now Pat. No. 7,139,077, which is a continuation of application No. 10/440,397, filed on May 19, 2003, now Pat. No. 6,927,860.

(51) Int. Cl.
*G01B 9/02* (2006.01)
*G01B 11/02* (2006.01)

(52) U.S. Cl. .................................................... 356/479

(58) Field of Classification Search ................. 356/479, 356/497, 511
See application file for complete search history.

(56) References Cited

U.S. PATENT DOCUMENTS

| 5,975,697 | A | 11/1999 | Podoleanu |
| 6,252,666 | B1 | 6/2001 | Mandella et al. |
| 6,618,152 | B2 | 9/2003 | Toida |
| 6,657,727 | B1 | 12/2003 | Izatt et al. |
| 6,760,769 | B2 | 7/2004 | Jayam |
| 6,769,769 | B2 * | 8/2004 | Podoleanu et al. .......... 351/221 |
| 6,927,860 | B2 * | 8/2005 | Podoleanu et al. .......... 356/479 |
| 7,102,756 | B2 | 9/2006 | Izatt et al. |
| 7,113,818 | B2 | 9/2006 | Podoleanu |
| 7,139,077 | B2 * | 11/2006 | Podoleanu et al. .......... 356/479 |
| 7,145,661 | B2 * | 12/2006 | Hitzenberger ............... 356/497 |
| 7,330,273 | B2 * | 2/2008 | Podoleanu et al. .......... 356/497 |
| 7,466,423 | B2 * | 12/2008 | Podoleanu et al. .......... 356/479 |

(Continued)

FOREIGN PATENT DOCUMENTS

WO WO0016034 A1 3/2000

(Continued)

*Primary Examiner*—Patrick J Connolly
(74) *Attorney, Agent, or Firm*—Lawrence E. Laubscher, Jr.

(57) ABSTRACT

OCT apparatus includes an interferometer, having an input beam splitter and a 50/50 output splitter. The splitting ratio of the input splitter may be optimized depending on the source power of light source and on the mismatch of the balanced receiver. The input splitter is a plate beam-splitter to minimize the stray reflected light in the interferometer and allow sequential operation of the apparatus in the OCT or in the confocal regime. The switching between the two regimes may be at will, or synchronous with the en-face scanning which results in quasi-simultaneous OCT/confocal imaging or in alternatives frames, confocal and OCT. By using polarization sensitive elements, two channels are provided in each regime, OCT and confocal. The two confocal polarization sensitive channels may allow adjustments of compensators prior to OCT measurements or OCT imaging.

30 Claims, 8 Drawing Sheets

U.S. PATENT DOCUMENTS

| | | | |
|---|---|---|---|
| 2002/0163622 A1* | 11/2002 | Magnin et al. | 351/212 |
| 2004/0036838 A1* | 2/2004 | Podoleanu et al. | 351/206 |
| 2004/0218189 A1 | 11/2004 | Izatt et al. | |
| 2004/0233457 A1* | 11/2004 | Podoleanu et al. | 356/479 |
| 2005/0174578 A1 | 8/2005 | Wei | |
| 2005/0231727 A1* | 10/2005 | Podoleanu et al. | 356/479 |
| 2005/0264820 A1* | 12/2005 | Podoleanu et al. | 356/479 |
| 2007/0019208 A1 | 1/2007 | Toida et al. | |
| 2007/0024868 A1 | 2/2007 | Izatt et al. | |
| 2007/0046948 A1* | 3/2007 | Podoleanu et al. | 356/497 |
| 2007/0076223 A1* | 4/2007 | Podoleanu et al. | 356/511 |
| 2007/0258095 A1* | 11/2007 | Olivier et al. | 356/479 |
| 2008/0088852 A1* | 4/2008 | Rogers et al. | 356/497 |
| 2008/0181477 A1* | 7/2008 | Izatt et al. | 382/128 |
| 2008/0285913 A1* | 11/2008 | Yang et al. | 385/24 |

FOREIGN PATENT DOCUMENTS

| | | |
|---|---|---|
| WO | WO0142735 A1 | 6/2001 |
| WO | WO0237075 A2 | 5/2002 |

* cited by examiner

US 7,535,577 B2

OPTICAL MAPPING APPARATUS WITH OPTIMIZED OCT CONFIGURATION

CROSS REFERENCE TO PRIOR APPLICATION

This application is a continuation of application Ser. No. 11/561,682 filed Nov. 20, 2006, now abandoned.

FIELD OF THE INVENTION

This invention relates to optical coherence tomography (OCT) configurations. In particular, the present invention provides configurations for optical mapping apparatus where optimized signal handling, particularly of light beams reflected and scattered back from an object, are easily attainable at reasonable cost.

BACKGROUND OF THE INVENTION

There are a number of patents and reports, which are noted below, which teach a variety of two splitter optical coherence tomography configurations. However, a difficulty that arises from nearly all of the prior devices is that there may be significant loss in the optics of the devices, and that there may be significant noise introduced into the device. Low losses in the OCT apparatus are required because of the low amplitude of the signal which is returned from the object or tissue that has been scanned. Moreover, OCT typically employs light sources which have significant bandwidth, giving rise to the presence of excess photon noise along with other noise items and sources such as shot noise and thermal noise.

Thus, an ideal OCT configuration should have low losses, while achieving good extinction or suppression of excess photon noise and/or derivations thereof, shot noise, and so on. In order to apply noise reduction, balance detection is employed, which requires an OCT configuration having a two splitter configuration.

It has been noted that a number of patents, which are identified below present various two splitter configurations, particularly for purposes of balance detection, but they pay little or no attention to the particular choice of splitting ratio of the splitters so as to minimize loss or to the particular choice of optical splitters to minimize the stray reflections in order to maximize the signal to noise ratio, and to allow multiple and versatile functionality.

As a practical matter, single mode couplers are preferred in OCT apparatus for routing the signal in order to project and define a desirable and controllable area or line on the target or object to be scanned. However, reflection from the end of the fiber leads may return light back into the system, thereby generating noise, and preventing the system from being used in a confocal scanning regime when the path of the reference beam is blocked.

In keeping with a particular aspect of the present invention, an improved optical mapping apparatus is provided which employs a bulk beam splitter having an optimized splitting ratio. A beam splitter having fiber input and output may be employed.

Thus, in a first aspect of the present invention, there is provided a two splitter OCT configuration which is powered by an optical radiation source having a large bandwidth, whereby balanced detection is achieved.

A second aspect of the present invention provides for an optical mapping apparatus having an OCT system which is built around a bulk beam splitter, wherein an input beam is split into an object beam and a reference beam, and where the object beam and reference beam are combined in a single mode fiber coupler.

As will be noted hereafter, a third aspect of the present invention provides methods and apparatus whereby en-face images of different depth resolution may be sequentially displayed.

A fourth aspect of the present invention discusses methods and apparatus which are sensitive to polarization of light returned from the object being scanned.)

In a fifth aspect of the present invention, methods and apparatus are discussed which can deliver, sequentially or quasi-sequentially, OCT images and confocal microscopy images.

DESCRIPTION OF THE PRIOR ART

The following patents and learned papers are referenced because, as noted, they provide discussion and teachings of various OCT and optical mapping apparatus configurations which, however, may have significant losses and inappropriate signal to noise ratios.

U.S. Pat. No. 5,268,738 Dec. 7, 1993 Baney et al
U.S. Pat. No. 5,321,501 Jun. 14, 1994 Swanson et al
U.S. Pat. No. 5,365,335 Nov. 15, 1994 Sorin
U.S. Pat. No. 5,491,524 Feb. 13, 1996 Hellmuth et al
U.S. Pat. No. 5,493,109 Feb. 20, 1996 Wei et al
U.S. Pat. No. 5,459,570 Oct. 17, 1995 Swanson et al
U.S. Pat. No. 5,644,642 Jul. 1, 1997 Kirschbaum
U.S. Pat. No. 5,975,697 Nov. 2, 1999 Podoleanu et al
U.S. Pat. No. 6,111,645 Aug. 29, 2000 Tearney et al
U.S. Pat. No. 6,252,666 Jun. 26, 2001 Mandella et al
U.S. Pat. No. 6,356,036 Mar. 12, 2002 Zhou
WIPO Publication WO 00/16034 Mar. 23, 2000 Izatt Takada et al "Phase-noise and Shot-noise Limited Operations of Low Coherence Optical Fine Domain Reflectometry" *Appl. Phys. Lett.* Nov. (1991), pp. 2483-2485.

Takada "Noise in Optical Low-Coherence Reflectometry" *IEEE J. Quantum Electron* Vol. 34 (1998), pp. 1098-1108.

Podoleanu et al "Noise Analysis of a Combined Optical Coherence Tomography and Confocal Scanning Opthalmoscope" *Appl. Opt.* 38 (10), (1999), pp. 2116-2127

Podoleanu "Unbalanced versus Balanced Operation in an OCT System" *Appl. Opt.*, January 2000, Vol. 39, No. 1, pp. 173-182.

K. Schoenberger et al "Mapping of birefringence and thermal damage in tissue by use of polarization-sensitive optical coherence tomography", *Appl. Opt.*, Vol. 37, No. 25, (1998), pp. 6026-6036.

The two Takada papers noted above each discusses the use of single mode couplers, but because of fiber end reflection there may be significant noise in the OCT system. The same fiber end reflection may also preclude the utilization of such systems in a confocal regime of operations.

U.S. Pat. No. 5,321,501 teaches a configuration that is based on two directional couplers. However, there is no discussion or contemplation of the influence of splitting ratios of the splitters on the performance of the system. Neither does the patent provide a means for choosing a splitting ratio.

Another two splitter configuration is shown in U.S. Pat. No. 5,268,738 which teaches a system which is designed to enlarge the OCT depth range by using multiple reflection lengths in the reference path of the interferometer. Once again, there is no discussion of choice of splitting ratios.

Another two splitter configuration, where the first splitter is a bulk splitter and the second splitter is a fiber splitter, is shown in U.S. Pat. No. 6,252,666. The purpose of the first splitter being a bulk splitter is to implement polarization splitting. Once again, there's no discussion of a splitting ratio.

Splitting ratios are discussed in the WIPO publication noted above. However, non-reciprocal devices such as circulators are used to route the signal, and those devices are very expensive. Moreover, there are no such circulators that are presently available which function in wavelengths of about 800 nm, which is a wavelength that is particularly employed in OCT applications relating to the human eye.

A problem which is common to most, if not all, of the patents noted above is that stray reflections may, and usually do, occur in the object arm, a problem which may come as a consequence of fiber end terminations or other elements within the system. Particular cases of optical coherence tomography, this may cause increased noise as a consequence of excess photon noise. This is the beat noise or phase noise due to the incoherent beating between the fiber end reflection or other stray reflectance in the object beam and the reference beam, as described in the Takada papers. If light reflected and scattered back from the target is to be monitored, the noise may exceed or even swamp the signal to be monitored. This problem is also discussed in the two Podoleanu papers noted above.

The U.S. Pat. No. 6,252,666 discuses a bulk beam splitter which is followed by a polarization maintaining fiber, but no mention is made or concern given to stray signals which come as a consequence of fiber end reflection. The WIPO publication discusses equations for determination of excess photon noise coming as a consequence of fiber end reflection, but provides no teachings of how to eliminate such noise.

The second paper by Podoleanu as noted above, "Unbalanced versus balanced . . . " discusses equations for quantification of excess photon noise coming as a consequence of fiber end reflection, but it provides no teachings of how to adjust the coupling ratio to maximize the signal to noise ratio. On the other hand, the WIPO publication presents equations for non-reciprocal configurations that are not applicable to simple directional couplers or bulk splitters.

In addition, all of the papers and patents noted above consider that balance detection is ideal, and the excess photon noise is cancelled and only the beat noise is left out of the excess photon noise as per the Takada papers. This limits the applicability of the equations derived. In practice, at high reference power values, the mismatch in the elements of the balanced receiver contributes to noise more than the noise due to the fiber end reflection. Due to different reasons, the balance detection may output an important term, a residual non-cancelled output of the excess photon noise. Deviations from the ideal balanced regime of operation are due to the electrical and optical parameters. Examples of electrical parameters are differences between the two photodetectors in terms of gain, noise and time response, as well as in the terms of the electronics processing the two signals out of the two photodetectors. Examples of optical parameters are optical delays between the two signals, launching of different optical modes in the two paths, as well as different spectrum contents or different polarizations of the wavelengths within the spectra of the two incident optical signals on the two photodetectors. No data exist as yet for the optimum of the splitters based on reciprocal devices used in OCT systems operating in different regimes than the shot noise.

A completely bulk two splitter system is taught in U.S. Pat. No. 5,975,697 which eliminates the fiber end reflection and allows operation of a sequential confocal system. However, it is been found in practice that the adjustment of two bulk beam splitters is difficult.

Additionally switching between OCT and confocal regimes of operation is via an optical screen. This requires time, and it would be desirable that the two images, OCT and confocal, be displayed simultaneously or for the switch to operate at a sufficient rate for the two images to be quasi-simultaneous.

It is also well known that the signal returned from birefringent tissue is processed with distortions by a simple OCT system, where due to inherent polarization properties of some of the optical components such as optical fibre and mirrors used at large angles, scattered waves with different polarization orientation are processed with different strengths. It would be desirable to eliminate these effects and/or to deliver polarization sensitive OCT images, or operate in the sequential regime as such is described in commonly owned U.S. Pat. No. 5,975,697, and to sequentially deliver polarization sensitive confocal images and polarization sensitive OCT images.

It is also well known that broadband light sources used in an OCT apparatus typically have a limited life, and therefore need frequent replacing. For example, the lifetime of a powerful 10 mW SLD may span several months of continuous use at maximum power. But that is all. Therefore, such sources—which typically have a pigtail connection—cannot be fused to the input fiber of the OCT apparatus, and an appropriate connector must be selected. Thus, pigtails are usually terminated with an FC/PC or FC/APC connector which, however, may introduce some losses into the system. Moreover, there may be reflection back from the connector, which is very detrimental to the SLD, and which at the same time may create a new source of noise.

A solution is therefore required, particularly so as to avoid reflections back to the broadband light source, and also to allow an easy replacement of the source when the power therefrom reduces in time below a certain level. It is also necessary to avoid the losses which are typically characteristic for fiber-fiber adapters.

Therefore, the present invention seeks to overcome the above disadvantages, providing configurations, circuits, methods of operation, and an easily controllable mapping apparatus which may be made available at reasonable cost and which has stability, ease of operation, and ease of maintenance, with increased versatility in comparison with existing implementations.

SUMMARY OF THE INVENTION

In accordance with one aspect of the present invention, there is provided an apparatus for optical coherence tomography, in which an optical beam is transferred through interface optics to an object to be scanned, and is reflected back therefrom for analysis. The apparatus comprises a source of low coherence or adjustable coherence light, an OCT interferometer, and image display means.

The interferometer comprises an output beam splitter having object beam and reference beam input ports, first and second photodetectors, and an input beam splitter having object beam and reference beam output ports.

The output beam splitter combines an object beam and a reference beam at its respective object beam and reference beam inputs, and is terminated at the first and second photodetectors so as to implement balance detection.

The input splitter transfers a proportion $1-\gamma$ of light that is input to it from the light source to the respective object beam output port, and the remainder $\gamma$ of the input light is transferred by cross transmission to the respective reference beam output port.

The light from the reference beam output port of said input splitter is directed to the reference beam input port of the output beam splitter.

Light reflected and scattered back from the object is output from the object beam output port of the input splitter and is reinjected into the object beam output port of the input splitter and is cross transmitted to the object beam input port of the output splitter.

The output splitter has a substantially 50/50 coupling ratio.

The splitting ratio $\epsilon=(1-\gamma)/\gamma$ of the input splitter may be optimized depending on the source power $P_S$ of the light source and on the mismatch of the operation of the balanced detection.

Typically, the object to be scanned has a safety limit level of power delivered thereto.

However, when the power $P_S$ of the light source is small so that shot noise and excess photon noise therefrom are negligible, and the power delivered to the object is at the safety limit level, then the splitting ratio $\epsilon$ is set as close as possible to 0, so that $1-\gamma$ is close to 1.

Moreover, when the power $P_S$ of the light source is small so that shot noise and excess photon noise therefrom are negligible, and the power $P_S$ is below a level whereby power delivered to the object is below the safety limit level, then the splitting ratio $\epsilon$ is set at approximately 1:2 so that about ⅓ of the optical source power $P_S$ is delivered to the object and about ⅔ of the optical source power $P_S$ is delivered to the reference path.

Still further, when the power $P_S$ of the light source is sufficiently high that a signal to noise ratio curve thereof versus the optical power therefrom will saturate, then the splitting ratio $\epsilon$ is set high so that the amount of optical power transferred to the object to be scanned is high and the amount of optical power delivered to the reference path is low.

Thus, an optimum attenuation of power in the reference path is sought so as to maximize the signal to noise ratio.

Typically, the input splitter is used in reflection by the reference beam and in transmission by the object beam.

However, the input splitter may be used in reflection by the object beam and in transmission by the reference beam.

The present invention also provides an optical mapping apparatus which comprises an OCT apparatus as described immediately above.

Thus such a mapping apparatus will comprise a source of low coherence or adjustable coherence light, an OCT interferometer, and image display means.

As described above, the interferometer comprises an output beam splitter having object beam and reference beam input ports, and an input beam splitter having object beam and reference beam output ports.

As before, the output beam splitter combines an object beam and a reference beam at its respective object beam and reference beam inputs, and is terminated with first and second photodetectors so as to implement balance detection.

Also, the input splitter transfers $1-\gamma$ of light that is input to it from the light source to the respective object beam output port, and the remainder $\gamma$ of the input light is transferred by cross transmission to the respective reference beam output port, once again so as to derive a splitting ratio $\epsilon=(1-\gamma)/\gamma$.

The light from the reference beam output port of the input splitter is directed to the reference beam input port of the output beam splitter.

Light reflected and scattered back from the object is output from the object beam output port of the input splitter and is reinjected into the object beam output port of the input splitter and is cross transmitted to the object beam input port of the output splitter.

In the mapping apparatus of the present invention, the input beam splitter may be a bulk beam splitter, and the output beam splitter is typically a single mode fiber coupler equipped with fiber ends that are cleaved at an angle at all inputs and outputs thereof.

The transverse scanning means comprises a line scanner and a frame scanner, whereby transverse scanning of an object is effected by an optical image beam that is output from the input beam splitter and is directed over a predetermined target position on the object.

The interface optics functions to transfer the optical imaging beam from the transverse scanning means to the object, and functions to transfer an optical output beam which is reflected and scattered back from the object to the input beam splitter through the transverse scanning means.

The focusing adjustment means is placed either between the input splitter and the transverse scanning means, or between the scanning means and the object to be scanned, so as to focus the optical imaging beam at a specific depth within the object.

The depth adjustment means functions to alter an optical path difference within the interferometer over a predetermined amount for at least one point in the transverse scanning means.

Also, the display means is adapted to generate and display at least an image created by the photodetectors.

In the optical mapping apparatus of the present invention, the transverse scanning means may be set to electively direct the optical imaging beam over a respective line or area of the object by respective operation of the line scanner or the frame scanner.

Moreover, the optical mapping apparatus of the present invention may further comprise modulation means to introduce signal modulation chosen from the group consisting of intensity modulation, phase modulation, and combinations thereof, in the interferometer.

If so, the interferometer may have air signal paths and fiber signal paths, and the modulation means is adapted to introduce signal modulation in the group of paths consisting of the air signal paths, the fiber signal paths, and combinations thereof.

In the optical mapping apparatus of the present invention, the depth adjustment means may function to alter the optical path difference in steps.

Alternatively, the depth adjustment means may function to alter the optical path difference continuously.

The optical mapping apparatus of the present invention may further comprise blocking means to block the reference beam, and an optical confocal receiver equipped with a summing amplifier for the first and second photodetectors.

Moreover, the respective images from the interferometer and the optical confocal receiver may be simultaneously displayed, and synchronized with the transverse scanning means.

In that case, display of a line in an image corresponds to movement of the line scanner, and advance of a line to completion of a predetermined area on the object which is being scanned corresponds to movement of the frame scanner.

When the optical mapping apparatus of the present invention is in use, the object has a depth axis, and the apparatus may further comprise a first timing means whereby en-face imaging of the object and longitudinal imaging of the object may be electively controlled.

In that case, the mapping apparatus may operate in an en-face imaging mode, in which case the apparatus acquires transverse images of the object at a constant depth.

However, when the mapping apparatus operates in a longitudinal imaging mode, the apparatus acquires longitudinal images of the object in a direction parallel to the depth axis.

The optical mapping apparatus of the present invention may be such that a confocal signal channel is established in the apparatus, and the object has a depth axis. The apparatus may then further comprise a second timing means.

Thus, when the reference beam is blocked, the second timing means controls the mapping apparatus so as to acquire transverse images at a constant depth in the confocal channel; or so as to acquire longitudinal images in the confocal channel. The depth of the images to be acquired is selected by adjustment of the focusing adjustment means.

Still further, the mapping apparatus may have an OCT signal channel and a confocal signal channel which are established in the apparatus.

Then, the first timing means controls an en-face mode, and the mapping apparatus acquires transverse images in a channel chosen from the group consisting of the OCT signal channel, the confocal signal channel, and combinations thereof.

Moreover, in the optical mapping apparatus of the present invention, the depth adjustment means in the interferometer and the focusing adjustment means may be simultaneously controlled so as to ensure that the image generated by the OCT interferometer and by the confocal receiver are selected from the same depth, and so that the signal strength in the OCT channel is at a maximum; and wherein constant depth scans from the same depth are acquired in both of the OCT channel and a confocal signal channel which is established in the apparatus.

The optical mapping apparatus of the present invention may be such that the bulk beam splitter is a plate beam splitter having a pair of parallel opposed surfaces.

In that case, the thickness of the plate is larger than the beam diameter divided by twice the value of the cosine of the angle between the beam and the orientation of the parallel opposed surfaces.

Also, one of the opposed surfaces may optionally have an antireflection coating thereon.

The optical mapping apparatus of the present invention may also be such that the outputs of the single mode fiber coupler are chosen from the group consisting of bare fibers cleaved at an angle, angled FC/APC connectors, angled ST/APC connectors, and combinations thereof.

Another feature of the OCT apparatus of the present invention may be that the light source has fiber output which is terminated with a polished connector that is cleared at an angle, or an FC/ARC connector, such that it can be screwed into a corresponding female receptacle, whereby light radiation from the light source may be fed to the input beam splitter.

The same may be true of the optical mapping apparatus of the present invention.

Also, in either of the OCT apparatus of the present invention or the optical mapping apparatus of the present invention, the input beam splitter may be a bulk beam splitter in the form of a plate, and the plate thereof has two opposed surfaces and sufficient thickness therebetween to laterally shift the two beams which are reflected by the two opposed surfaces so as to permit the beam reflected by one of the two opposed surfaces to be directed out a respective output port thereof, while the beam from the other of the two opposed surfaces is ignored, and is thus not allowed to couple to the rest of the system.

A further embodiment of the present invention provides an optical mapping apparatus which comprises an OCT apparatus wherein an optical beam is transferred to an object to be scanned through interface optics and is reflected back therefrom through an OCT channel for analysis, a transverse scanning means, focusing adjustment means, analyzing means, depth adjustment means, and image display means, all as noted above. However, in this embodiment the OCT apparatus comprises a source of low coherence or adjustable coherence light, a V OCT interferometer and an H OCT interferometer.

Light from the source is prepared by a polarizer as a linear state input to the two OCT interferometers.

The V and H interferometers share an input splitter having object beam and reference beam output ports.

The V interferometer further comprises an output splitter V having an object beam input port and a reference beam input port; and likewise the H interferometer further comprising an output splitter H having an object beam input port and a reference beam input port.

The output beam splitter of the H interferometer combines an object beam and a reference beam at its respective object beam and reference beam inputs, and has a pair of photodetectors H at its output, so as to implement balance detection, with maximum sensitivity for the horizontal orientation of polarization of the object beam, and to deliver an output OCT H image.

Likewise, the output beam splitter of the V interferometer combines an object beam and a reference beam at its respective object beam and reference beam inputs, and is terminated on a pair of photodetectors V so as to implement balance detection, with maximum sensitivity for the vertical orientation of polarization of the object beam, and to deliver an output OCTV image.

As before, the input splitter transfers $1-\gamma$ of light input to it from the light source to the respective object beam output port, and the remainder $\gamma$ of the input light by cross transmission to its respective reference beam output port so as to derive a splitting ratio $\epsilon=(1-\gamma)/\gamma$.

The light from the reference beam output port of the input splitter is directed to a reference polarization beam-splitter via a retarder so as to adjust the polarization state to a linear orientation at 45° from the axes of the reference beam splitter, whose outputs are sent to the reference beam input ports of the output beam splitters in the two interferometers.

Also, the polarization state of the light from the object beam output port is prepared in an arbitrary polarization by a variable compensator before being launched into the transverse scanning means.

Light reflected and scattered back from the object is output from the object beam output port of the input splitter and is injected into the object beam output port of the input splitter and is cross transmitted to an object polarization beam-splitter whose different polarization outputs are coupled to the object beam input ports of the two output splitters in the two interferometers.

The input splitter is a bulk beam splitter in the form of a plate, and the output splitters are single mode fiber couplers equipped with fiber ends that are cleaved at an angle at all inputs and outputs thereof.

The output splitters have polarization controllers to maximize the signal received at their respective object and reference input ports, and the two output splitters are adapted to process orthogonal linear states of polarization.

Moreover, the transverse scanning means comprises a line scanner and a frame scanner. Thus, transverse scanning of an object is effected by an optical image beam that is output from the input beam splitter and is directed over a predetermined target position on the object.

Still further, the interface optics functions to transfer the optical imaging beam from the transverse scanning means to the object, and functions to transfer an optical output beam which is reflected and scattered back from the object to the input beam splitter through the transverse scanning means.

Also the focusing adjustment means is placed either between the input splitter and the transverse scanning means, or between the transverse scanning means and the object to be scanned, so as to focus the optical imaging beam at a specific depth within the object.

The depth adjustment means functions to alter the optical path difference synchronously for both of the interferometers over a predetermined amount for at least one point in the scanning raster, and the same optical path difference in both OCT interferometers is substantially maintained all the time.

Thus, the display means is adapted to generate and display at least two simultaneous images created by the respective pairs of photodetectors. In this manner, a polarization insensitive image OCTI, is generated according to the formula: $OCTI = [(OCTV)^2 + (OCTH)^2]^{1/2}$, and the phase retardation $OCT\phi$ in the tissue of the object to be scanned, up to the investigated depth, is obtained by a method chosen from the group consisting of evaluating $OCT\phi = \arctan(OCTV/OCTH)$, and using logarithmic amplifiers according to the formula $OCT\phi = \arctan\{\exp[(\log(OCTV) - \log(OCTH)]\}$.

The optical mapping apparatus as described above may further comprise blocking means to block the reference beam before the reference polarization beam-splitter, and an optical confocal receiver H for the output splitter H and an optical confocal receiver V for the output splitter V, each equipped with a summing amplifier for the respective pair of photodetectors.

Here, there are output signals CONFOCALV and CONFOCALH from the confocal receiver V and the confocal receiver H, respectively, which are obtained when the reference beam is blocked, and are used to produce a polarization insensitive confocal image CI=[CONFOCALH+CONFOCALV] and a phase retardation map $CONFOCAL\phi$ in keeping with a method chosen from the group consisting of evaluating $CONFOCAL\phi = \arctan(\sqrt{CONFOCALV/CONFOCALH})$ and using logarithmic amplifiers to evaluate $CONFOCAL\phi = \arctan\{\exp[0.5(\log(CONFOCALV) - \log(CONFOCALH))]\}$.

Still further the respective OCTH images from the H interferometer, produced by the respective H pair of photodetectors are simultaneously displayed with the respective images OCTV from the V interferometer, which are produced by the respective V pair of photodetectors, and the pairs of images are synchronized with the transverse scanning means.

The polarization insensitive image OCTI, and the phase retardation $OCT\phi$ may be optionally displayed simultaneously, or optionally the OCTV, OCTH, OCTI, and $OCT\phi$ images, and combinations thereof, may be optionally displayed simultaneously, so that display of a line in an image corresponds to movement of the line scanner, and advance of a line to completion of a predetermined area on the object which is being scanned corresponds to movement of the frame scanner.

Also, in keeping with the present invention, the respective images CONFOCALH from the H optical confocal receiver, are simultaneously displayed with the respective images CONFOCALV from the V optical confocal receiver, or optionally the OCTV, OCTH, OCTI, and $OCT\phi$ images, and combinations thereof, may be optionally displayed simultaneously, and the respective pairs of images are synchronized with the transverse scanning means.

Thus, display of a line in an image corresponds to movement of the line scanner, and advance of a line to completion of a predetermined area on the object which is being scanned corresponds to movement of the frame scanner.

Still further, at least one of the respective images CONFOCOLH and CONFOCALV, and combinations thereof, are simultaneously displayed with at least one of the respective images OCTV and OCTH, and combinations thereof, and the respective pairs of images are synchronized with the transverse scanning means.

Once again, display of a line in an image corresponds to movement of the line scanner, and advance of a line to completion of a predetermined area on the object which is being scanned corresponds to movement of the frame scanner.

In another variation of the optical mapping apparatus described above where the object has a depth axis, the apparatus may be electively controlled to operate in an en-face imaging mode or in a longitudinal imaging mode.

In the en-face mode, the mapping apparatus acquires transverse (C-scan) images of the object at a constant depth in:
(i) both OCT interferometers H and V by changing the optical path in both interferometers simultaneously employing the depth adjusting means, and
(ii) both confocal receivers H and V by operating the focusing adjustment means.

Moreover, in the longitudinal imaging mode, the mapping apparatus acquires images of the object in a direction parallel to the depth axis (B-scan) in:
(i) both OCT interferometers H and V by changing the optical path in both interferometers simultaneously employing the depth adjusting means, and
(ii) both confocal receivers H and V by operating on the focusing means.

In the optical mapping apparatus described above, the depth adjustment means in the interferometers, and the focusing adjustment means, are simultaneously controlled so as to ensure that the images generated by the OCT interferometers and the confocal receivers are selected from the same depth, and that the signal strength in the OCT channels is at a maximum.

Typically, the variable compensator in the object path produces light which is circularly polarized.

Moreover, the variable compensator may be adjusted to compensate for the birefringence of a first part of the object in transverse section, by using information acquired in the confocal imaging regime in order to obtain OCT image and OCT information from a second part of the object in transverse section.

In various embodiments of the present invention, the blocking means are implemented by using a chopper or an optical modulator, operated in synchronism with the scanner so as to generate a line in a final raster in such a way that the time interval of blocking the beam starts and stops in antiphase with the time interval of allowing the beam through, and such that starts and stops are synchronized with the moment when the line scanner changes the direction of movement.

Here, each frame consists of two images, one OCT and the other confocal, where half of the line in each raster bears useful image information while the other half is disregarded or discarded, and each useful half of the lines in the image produced by the OCT channel corresponds to scanning the beam transversally from one extreme to the other in one direction while the useful half of the lines in the confocal image is created during such movement in the opposite direction.

An alternative arrangement is such that the blocking means are implemented by using a chopper or an optical modulator, operated in synchronism with the scanner so as to generate a frame in a final raster in such a way that the time interval of blocking the beam starts and stops in antiphase with the time interval of allowing the beam through, but such that starts and stops are synchronized with the moment when the frame scanner changes the direction of movement and during each frame, only one alternate OCT or confocal image is useful, while the subsequent frame in the respective OCT channel or confocal channel is disregarded or discarded.

Each useful frame produced by the OCT channel corresponds to scanning the beam transversally from one extreme to the other in one direction while the useful frame produced by the confocal channel is created during such movement in the opposite direction.

In either variation noted immediately above, the OCT image comprises at least two OCT images, and the confocal image comprises at least two confocal images provided by polarization sensitive channels and combinations thereof.

A further variation of optical mapping apparatus in keeping with the present invention is where the information collected in a confocal imaging regime is used for a purpose such as to guide the imaging in a successive or quasi-simultaneous OCT regime of operation, or for the adjustment of the object to be scanned prior to OCT imaging, or for identification of borders below a speckle threshold in the OCT image.

In yet another embodiment of the present invention, an optical mapping apparatus is provided which, as before, comprises an OCT apparatus wherein an optical beam is transferred to an object to be scanned through interface optics and is reflected back therefrom through an OCT channel for analysis, a transverse scanning means, focusing adjustment means, analyzing means, depth adjustment means, and display means.

As before, the OCT apparatus comprises a source of low coherence or adjustable coherence light, two OCT interferometers, and image display means.

The interferometers share an input splitter having object beam and reference beam output ports.

Each of the interferometers comprises an output splitter having an object beam input port and a reference beam input port.

Also, each of the output beam splitters combines an object beam and a reference beam at its respective object beam and reference beam inputs, and is terminated on a pair of photodetectors so as to implement balance detection.

Once again, the input splitter transfers $1-\gamma$ of light input to it from the light source to the respective object beam output port, and the remainder $\gamma$ of the input light by cross transmission to its respective reference beam output port so as to derive a splitting ratio $\epsilon=(1-\gamma)/\gamma$.

Here, the light from the reference beam output port of the input splitter is directed to a reference non-polarizing beam-splitter whose outputs are sent to the reference beam input ports of the output beam splitters in the two interferometers.

Then, light reflected and scattered back from the object is output from the object beam output port of the input splitter and is injected into the object beam output port of the input splitter and is cross transmitted to an object non-polarizing beam-splitter whose outputs are sent to the object beam input ports of the two output splitters in the two interferometers.

Here, the input splitter is a bulk beam splitter in the form of a plate, and the output splitters are single mode fiber couplers equipped with fiber ends that are cleaved at an angle at all inputs and outputs thereof.

The output splitters have polarization controllers to maximize the signal received at their respective object and reference input ports.

Also, the transverse scanning means comprises a line scanner and a frame scanner, whereby transverse scanning of an object is effected by an optical image beam that is output from the input beam splitter and is directed over a predetermined target position on the object.

As before the interface optics functions to transfer the optical imaging beam from the transverse scanning means to the object, and functions to transfer an optical output beam which is reflected and scattered back from the object to the input beam splitter through the transverse scanning means.

However, here the depth adjustment means functions to alter the optical path difference synchronously for both the interferometers over a predetermined amount for at least one point in the transverse scanning means while a chosen value for the offset between the optical path differences in the OCT interferometers is substantially maintained all the time.

In this case, the focusing adjustment means has a depth of focus which is larger than the offset, and may be placed either between the input splitter and the transverse scanning means, or between the transverse scanning means and the object to be scanned.

The display means is adapted to generate and display at least two simultaneous images created by the respective pairs of photodetectors.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion.

A number of the prior art patents that have been noted above teach these techniques, and OCT apparatus that can be constructed in bulk or optical fiber. For example, each of the following United States patents teaches such a system: U.S. Pat. Nos. 5,459,570; 5,321,501; 5,491,524; 5,493,109; 5,365,335; 5,268,738; and 5,644,642. Each of these teaches OCT systems that have means for transversely scanning a target, means for longitudinal scanning of the reference path length, means for phase modulation, means for controlling the polarization state of the beam as bulk or fiber polarizer controls, and means for compensating for the dispersion.

Figure 1:
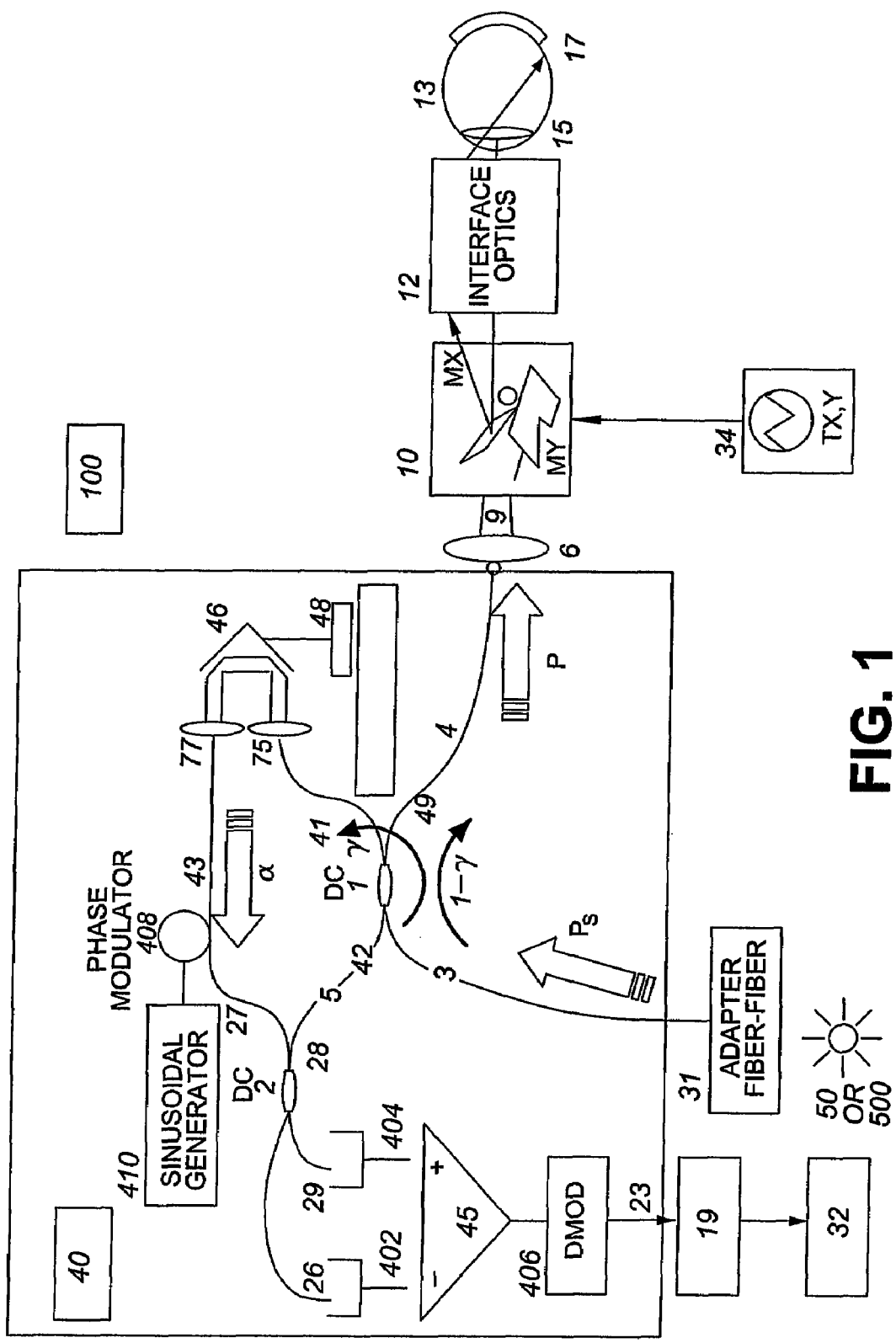
FIG. 1 shows, in diagrammatic form, the main elements of a two-splitter OCT system, and the manner in which a pigtailed broadband source is coupled to the OCT system.

Referring to FIG. 1, there is diagrammatically shown an OCT apparatus having a two coupler configuration. Such configuration is not dissimilar to that which is known from the prior art, such as U.S. Pat. No. 5,321,501. Particularly, the main elements that are shown in FIG. 1 are similar to those of an optical mapping apparatus having adjustable depth resolution such as that which is taught in U.S. Pat. No. 5,975,697 which has common ownership with present invention. The apparatus 100 includes an OCT interferometer 40 which is excited by a source of light which can have either low coherence, such as light source 50; or the source may be one having an adjustable coherence length, indicated by the reference numeral 500.

In the context of the present invention, a source having low coherence may be considered to be a broadband source, being one whose coherence length is much less than the penetration depth of radiation used in the object being studied. Such sources may be superluminescent diodes (SLD), tungsten lamps, Kerr-lens mode-locked lasers, laser diodes below threshold, and combinations of the above. The known technology as that the date filing of the present application is such that the coherence length of such sources is typically in the range 0.001 to 1 mm.

However, in the context of the present invention, a high coherence source is considered to be one that has a coherence length that is much larger than the penetration depth of the radiation used in the object being studied. Typically, such sources may be lasers, having a coherence length of over 0.1 mm.

In the configuration of FIG. 1, and also the other figures which are and will be referred to hereafter, the same reference numerals are used for the same elements. Moreover, where identical elements are duplicated in several of the figures, the duplicate element will be typically indicated by the same reference numeral having a "prime" indicator along with it.

The interferometer 40 includes an input splitter 1 and an output splitter 2 which is terminated on the photo detectors 402 and 404 in a balanced detection configuration. The input splitter 1 has input ports 3 and 42, and outputs 41 and 49. The output splitter 2 has two inputs; an object input 28 and a reference input 27, at which the respective object and reference beams are injected. There are also the two output ports 26 and 29 for the output splitter 2, which lead to the photodetectors 402 and 404, respectively. The port 42 of the splitter 1 feeds the input 28 of the splitter 2.

An OCT sample beam 4 is output from the splitter 1 of the OCT interferometer 40, using single mode fiber if the OCT interferometer is in fiber. However, if the OCT interferometer is in bulk, or when at least splitter 1 is in bulk, the reference numerals 4, 5 and 43 indicate a free space optical beam.

The optical source 50 or 500 is tied to the input 3 of the input splitter 1. The output port 41 of the input splitter 1 injects light into the reference path 43. If the source 50 or 500 is pigtailed, then it is quite common for it to be fused up to the input 3 of the input splitter 1. However, if apparatus in keeping with present invention is to be delivered to a purchaser in the field, then such an arrangement is not acceptable as it does not permit for an easy source replacement. Therefore, typically a commercial system in keeping with the present invention will be delivered with a fiber-fiber adapter 31, such as an ST/ST adapter or an FC/FC adapter, or equivalent, as well known to those skilled in the art relating to fiber technology and to those having experience in the OCT field.

It is also well known in the fields mentioned above that optical sources are sensitive to reflections, and therefore such sources are equipped by manufacturers with angled connectors. However, adapters between FC/APC connectors—which are connectors that are cleaved at an angle between four degrees and eight degrees—may cause high injection losses.

The OCT sample beam at the output 49 of the input splitter 1 is delivered by the fiber 4, or by a free space optical output beam as noted above, and is focused by an optical element 6. Typically, the optical element 6 is such as a reflective or refractive optical element into a beam 9 which is then deflected by a two-dimensional scanner head 10 so as to scan transversely, via the interface optics 12, a target object 13. Typically, particularly in OCT configurations and applications in keeping with the present invention, the object is the retina 17 of an eye 13; and the beam is focused by the eye lens 15 onto the retina (object) 17.

The scanner head 10 has a scanning assembly which is typically one that is well known in the art. The scanner head 10 may be, for example, a galvanometer scanner, a polygon mirror, a resonant scanner, an acousto-optic modulator, a piezo-vibrator, a rotating or vibrating prism, and so on. The scanner head 10 may typically be under the control of a triangle, saw-tooth, or DC voltage, any of which may be produced by a generator 34. The scanner head 10 can be divided into two parts, namely a line scanner and a frame scanner, which are separated by optical elements such as lenses and/or mirrors in configurations that are well known in the scanning laser opthalmoscopy (SLO) art. The scanning head 10 may also comprises confocal microscopy or general raster scanning systems, in which case the scanner head 10 and the interface optics 12 are interleaved one with the other in a single block. However, for the sake of convenience, they are represented separately in FIG. 1.

The scanner mirrors MX and MY may be mirrors such as those employed in galvanometer scanners, polygon mirrors, resonant scanners, and the like, which have a high reflectivity at the wavelength used. However, if acousto-optic modulators or prisms are used, then their transmission at the wavelength used is high. It is well known in the art for two scanners to have orthogonal axes, or to scan the beam in perpendicular planes so as to produce a raster in the X,Y plane which is oriented perpendicular to the optical axis of the system. It is also known to produce a circular scan (r,q) of the beam, which can be obtained by sinusoidally scanning the beam using the two scanners in orthogonal directions at the same frequency with a phase difference of π/2, where r is determined by the amplitude of the angular deviation, measured in a plane which is perpendicular to the optical axis of the system from the point on the target upon which the beam is incident when scanners are not driven; and q is a polar angle in this plane. Typically, one of the scanners works fast, and the signal collected during its movement is displayed on the line in the raster. If so, such scanner is determined to be the line scanner. The other scanner is slower, and moves the lines in a direction perpendicular to the line orientation, and is therefore determined to be a frame scanner.

Of course, combinations of scanners such as the various ones that have been discussed above can be employed in the scanner head 10. For example, a polygon mirror may be employed as the line scanner and a galvanometer scanner may be employed as the frame scanner.

It will be obvious to those skilled in the art that the scanner head may consist of only one transverse scanner operating simultaneously closing two directions perpendicular one to the other. In this case, movement in one direction replaces the movement imported by the mirror MX, and movement in the other direction replaces the movement imparted by the mirror MY.

The paths 4 and 9, together with the scanning head 10 and the interface optics 12 and lens 15, define an object path along which the object signal is returned.

The object signal interferes with the reference signal when the optical path difference (OPD) between the reference path and the object path is less than the coherence length of the source 50 or 500. Thus, depth selection of the OCT is attainable; and it is understood that points along the object beam in the volume of the object will contribute to the signal only from within the coherence length of the source in the substance of the object.

The light which is returned by the object is reflected and scattered, and is partly collected via the focusing element 6 back into the output 49 of the input splitter 1, and thence to the object input 28 of the output splitter 2. Focusing elements 75 and 77 are employed in paths 41 and 43 for the well known purposes.

A sinusoidal generator 410 may typically be employed together with a phase modulator 408. The reference numeral 46 indicates a corner cube or a pair of mirrors whose particular purposes described hereafter with respect to FIG. 2. Likewise, the particular purposes for the demodulator 406, the output OCT signal 23, and the differential amplifier 45, are discussed in detail hereafter with reference to FIG. 2.

It will be understood, in any event, that the output OCT signal 23 may be displayed and be recorded by a suitable display device 19, which may be such as a frame grabber, a storage oscilloscope, or a suitable printer. The display device may be under the control of a computer 32.

The depth in the OCT channel is scanned by changing the optical path in the object or reference beam of the interferometer 40, using depth scanning means 48 which are controlled by the computer 32. Alternatively, the depth scanning means 48 may be controlled by galvanometer scanners in configurations of lenses such as those taught in commonly owned U.S. Pat. No. 5,975,697. Of course, other means to control the movement of a mirror or groups of mirrors or prisms are known to those skilled in the art; and galvanometer scanners and gratings may be employed as is discussed in U.S. Pat. No. 6,111,645.

However, as noted above, none of the known patent disclosures discloses criteria applicable to the OCT configuration of FIG. 1, by which the splitting ratios of the two splitters, the input splitter 1 and the output splitter 2, may be optimized. Several optional cases, and solutions, are presented by the present invention with respect to optimization of splitting ratios.

In order to understand the teaching behind different options, there follows below a brief signal to noise analysis applicable to FIG. 1. This uses similar notations as those used in the second above-noted Podoleanu paper. The power to the object is $P_S$ the object reflectivity is O, the photodetector responsivity is α, and the attenuation of the light reinjected back into the reference input port of the output splitter 2, i.e. into the fibre is described by σ. The cumulative reflectivity for the amount of light reflected by the fiber end in the object arm is R. The shot noise photocurrent due to the object is neglected in comparison with the shot noise due to the reference power (O<<σ). The receiver noise is considered to be dominated by thermal noise and the splitters 1 and 2 are considered loss-less.

σ is generally large, so for simplicity we neglect R in comparison with σ. The accumulated photocurrent due to the fiber end reflection is $<I_{FER}>$. The accumulated photocurrent due to the reference signal is $<I_{REF}>$:

$$<I_{REF}> \approx \alpha\sigma\frac{\gamma}{1-\gamma}P \tag{1a}$$

$$<I_{FER}> \approx \alpha R\gamma P \tag{1b}$$

The signal to noise ratio can be written as:

$$\frac{S}{N} = \frac{GP^2}{(AP^2 + DP + C)B} \tag{2}$$

where: B is the electrical bandwidth $$G = 2(\alpha\gamma)^2 O \tag{3a}$$

$$A = 2\alpha^2(1+\Pi^2)(\Delta\nu_{eff})^{-1}\gamma^2\left[R + \frac{m\sigma}{1-\gamma}\right] \tag{3b}$$

$$D = 2e\alpha\gamma \tag{3c}$$

$$C = \frac{1-\gamma}{\sigma}<\Delta I_a^2>/B = \frac{4kT}{R_L}\frac{1-\gamma}{\sigma} \tag{3d}$$

and: $\Delta\nu_{eff}$ and Π are the effective noise line width and polarization of the source, respectively.

In addition to the analysis in Podoleanu paper, an extra noise term due to mismatch in the balanced detector is considered in (3b). Deviations from ideal balanced condition result in an un-cancelled excess photon noise term. The term is written as the excess photon noise, mainly determined by the reference photocurrent, multiplied by the mismatch coefficient m. It will be seen immediately that the optimization of the first splitter ratio, γ, is different from the case when the balanced detector was ideal (m=0) and the only excess photon noise term is that due to the beat noise, or photon noise proportional with the fiber end reflection R.

It is obvious the effect that σ and γ have now in reducing the receiver noise. The larger γ and σ, the lower the receiver noise contribution. With γ and σ close to 1, C can be diminished significantly.

There are several different cases to be considered:

Case 1a. In the first case, it is assumed that the power of the optical source 50 or 500 is sufficiently small for the shot noise and excess photon noise to be negligible, the OCT configuration has to operate fast, and the power to the object is at the safety limit level.

An example could be a fast OCT apparatus working in A-scan regime for the cornea. In this case, the load resistor $R_L$ has to be small for fast acquisition which determines a high thermal noise. At the same time, the beam is not scanned and the safety limit requires for instance in the case of the eye, a few or tens of μW. In this case, the thermal noise ratio becomes:

$$\frac{B}{O}\frac{S}{N} = \frac{GP^2}{C} = \frac{(\alpha\gamma)^2 P^2}{\frac{4kT}{R_L}\frac{1-\gamma}{\sigma}} \tag{4}$$

In order to ensure a high efficiency in using the signal, it is important that the input splitter 1 shall have an optimized splitting ratio of the forward transmission $1-\gamma$, which comes from the input 3 to the output 49, with respect to the cross transmission γ to the reference path output 41. The signal to noise ratio reaches a maximum when γ tends to 1. An optical splitter with 10% power transferred to the object and 90% to the reference power is an example of this case.

Case 1b. In the second case, it is assumed as before that the power of the optical source 50 or 500 is sufficiently small for the shot noise and excess photon noise to be negligible, the OCT configuration has to operate fast, but the optical source is not capable of delivering power to the object up to the safety limit.

In this case, the condition (4) changes. The source power is $P_S$:

$$P_S = \frac{P}{1-\gamma} \tag{5}$$

and (2) becomes:

$$\frac{B}{O}\frac{S}{N} = \frac{\sigma(\alpha\gamma)^2(1-\gamma)P_S^2}{\frac{4kT}{R_L}} \tag{6}$$

In order to ensure a high efficiency in using the signal, it is important that the input splitter 1 shall have an optimized splitting ratio of the forward transmission $1-\gamma$, which comes from the input 3 to the output 49, with respect to the cross transmission γ to the reference path output 41. Expression (6) has a maximum at $\gamma=2/3$, i.e 1/3 from the source power shall be transferred by the optical splitter 1 to the object output port and 2/3 from the source power shall be transferred to the reference output beam.

Case 2a. A third case assumes that the balance detection is ideal, which together with a moderate power safety level makes the shot noise dominate over the excess photon noise, and also that the safety level is as such that the receiver noise can also be neglected in comparison to the shot noise and additionally that the power to the object is at the safety limit level.

For example, when the power P increases, such as for scanned en-face imaging, where the safety value could be as high as 1 mW to the eye, the receiver noise could be ignored in comparison with the shot noise. DPB in (3c) dominates over CB in (2). When R and m are small, DPB also dominates over $AP^2$ in (2) and the signal to noise ration becomes:

$$\frac{B}{S}\frac{S}{N} = \frac{GP}{D} = \frac{\alpha\gamma P}{e} \tag{7}$$

Again, the larger γ the larger the signal to noise ratio.

Another case assumes as immediately above that the balance detection is ideal which together with a moderate power safety level makes the shot noise dominate over the excess photon noise and also that the safety level is as such that the receiver noise can also be neglected in comparison to the shot noise but in opposition to the case immediately above, the power of the source cannot deliver the safety power level to the object.

Such a case is the en-face OCT imaging of skin in which case the safety power level P can be as high as tens of mW, then, using (5)

$$\frac{B}{O}\frac{S}{N} = \frac{GP}{D} = \frac{\alpha\gamma(1-\gamma)P_S}{e} \tag{8}$$

which reaches maximum for γ=0.5.

A different reported case assumes that the optical power is so large that the signal to noise ratio curve versus optical power saturates due to a significant value of the stray reflectances in the system, and that balanced detection is ideal.

This happens at safety powers P of over a few hundreds of μW to mW, when $ABP^2$ in (3b) dominates. As supposed in this case, balance detection works close to the ideal cancellation regime of the excess photon noise, and the expression (2) saturates to a maximum given by:

$$\left(\frac{B}{S}\frac{S}{N}\right)_{max} = \frac{G}{A} = \frac{\Delta v_{eff}}{R(1+\pi^2)} \tag{9}$$

This is the equation obtained in the Podoleanu paper noted above, based on the ideal balanced detection, as stated in the Takada papers. The equation (9) requires as small a R as possible.

A fourth case which is a subject of this disclosure supposes, as does the case immediately described above, that the optical power is so large that the signal to noise ratio curve versus optical power saturates; but as a difference to the case immediately above, due to a non-ideal balanced detection scheme. Due to a balance detection mismatch, the excess photon noise is larger than that due to the stray reflectances in the system. This is also the case when no such stray reflectances exist.

FIGS. 2 and 4 to 6 show implementations of OCT configurations where the splitter 1 has no fiber end reflection. It was also noticed in practice that the limit as described by equation (9) could not be achievable. This is due to the deviations of the balanced detector from ideal cancellation of all excess photon noise, i.e. to a case described by m different from zero in (3 a). Expression (9) changes to:

$$\left(\frac{B}{O}\frac{S}{N}\right)_{max} = \frac{G}{A} = \frac{(1-\gamma)\Delta v_{eff}}{m\sigma(1+\Pi^2)} \quad (10)$$

Expression (10) requires a small γ and attenuation of the reference beam, expressed by σ (as long as ABP² remains dominant, a decrease of σ results in an increase of the thermal noise). In order to ensure a high efficiency in using the signal, it is important that the input splitter 1 shall have an optimized splitting ratio of the forward transmission 1−γ as high as possible, together with attenuation of the power in the reference path. An optical splitter with 90% power transferred to the object and 10% to the reference power is an example of this case. In this case, a variable attenuator is introduced into the reference path to maximize the signal to noise ratio. Experimentally, the attenuation is increased until the signal to noise ratio attains a maximum. The signal power is proportional with σ while the noise power is proportional to σ². However, by reducing σ, other noise terms such as the shot noise and the thermal noise will become non-negligible. This suggests that σ cannot be made infinitesimally small and an optimum exists.

Attenuation can be introduced using means known in the art, such as a bulk variable attenuator, or by de-focusing the light launched into the reference input beam of the splitter 2, or by shifting the reference input beam of the splitter 2 laterally.

It will thus be appreciated that maximum efficiency can be obtained without having to resort to the use of expensive optical circulators such as those described in the WIPO publication referred to above, so long as the target is not very reflective and does not return sufficient power into the optical source to generate noise or destroy it.

In any event, it has been determined that the output splitter needs to have a ratio of substantially 50/50 in order to ensure optimum balance detection operation. However, this is difficult to achieve in practice for all wavelengths within the spectrum of the optical source, especially for large bandwidth sources (over 50 nm). Deviations from 50/50 for frequencies outside the central wavelength of the single mode coupler being used will contribute to an increased value for the coefficient m in (3b).

Or it will be obvious to those skilled in the art, of course, that the configurations such as that shown in FIG. 1, may be implemented with both of the input and output splitters 1 and 2, respectively, being fiber splitters; or alternatively, either the splitters may be in bulk and the other in fiber, or both in bulk. Of course, the splitting ratio ε for the input splitter should be optimized as described above, with the splitting ratio of the output splitter close to 50/50 for most frequencies within the source spectrum.

Figure 2:
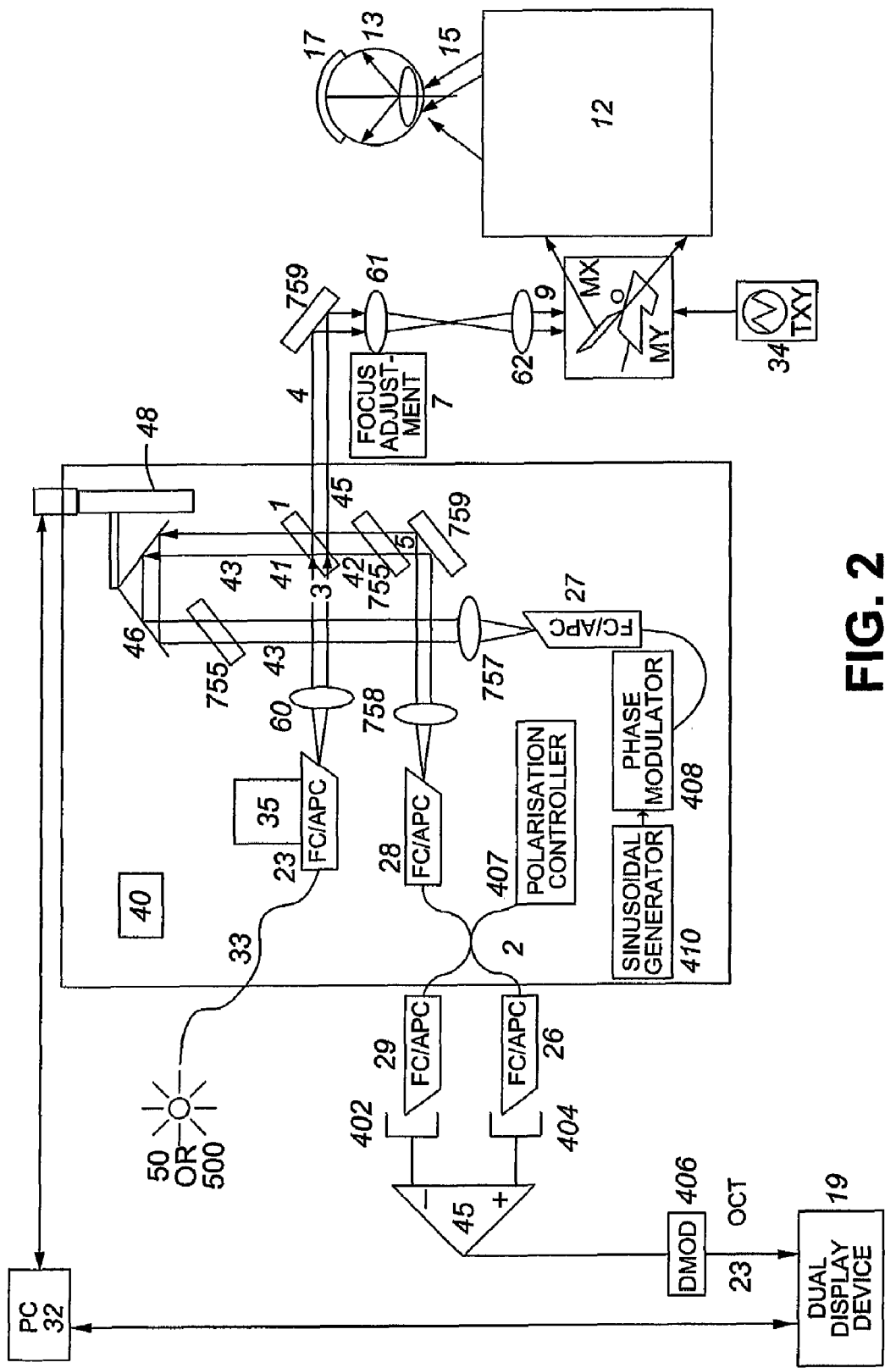
FIG. 2 shows, in diagrammatic form, a first specific embodiment of an optical mapping apparatus in keeping with present invention.

Turning now to FIG. 2, there is shown an optimized configuration of a two optical splitter configuration which is in keeping with present invention. It will be understood that the pigtailed source 50 or 500 is equipped with a fiber 33 that is terminated at an angled connector 23. It has been noted above that the connector 23 may be an angled connector such as ST/APC or FC/APC, or other suitable connector as those skilled in the art may determine. In any event, the connector 23 is screwed into the mount 35 so that light is launched into the input of the splitter 1 along the path of 3. A focusing element 60 may be employed, as required.

One output 49 of the input splitter 1 is launched to the object beam 4, which scans the object 13, 17, while the other output 41 is launched into the reference path and beam 43, which is reflected by the corner cube 46—which may also be two mirrors.

This arrangement may allow movement up to 2 cm; and this allows a change of the optical path in the reference path by means which are known in the OCT art, where the corner cube or mirrors 46 are attached to the translation stage 48 under the control of computer 32.

It will also be noted that the reference beam 43 is focused by a focusing element 757 into the reference input 27 of the output splitter 2. The output splitter 2 uses a single mode directional coupler. The fiber tips of the directional coupler employed in the output splitter 2 are cleaved at an angle so as to ensure small values for any stray reflections that may occur in the system. Of course, it is understood that such stray reflections, if large, may contribute significantly to noise within the system.

Alternatively, the lens 757 and the input fiber 27 may be positioned so as to sit on a translation stage 48, which may be such as a small coil of fiber between the input fiber 27 and the output splitter 2.

Alternatively, the fiber ends 23, 26, 27, 28, 29, may be terminated with angled connectors such as FC/APC or ST/APC connectors.

It will also be noted that the photodetectors 402 and 404 may be pin type, or they may be avalanche photo diode types (APD).

The input splitter 1 has a splitting ratio ε, as described above; and will be understood that the splitting ratio ε can be optimized using the relations described above. In FIG. 2 there is shown an implementation where the input splitter 1 is used in transmission by the object beam 9, and in reflection by the reference beam 43. It will be recognized by those skilled in the art that equivalent implementation, where the input splitter 1 is used in reflection by the object beam 9 and in transmission by the reference beam 43 is also possible.

In any embodiment of the present invention, a dispersion compensator 755 may be interleaved in interferometer 40, in one of the paths, such as object paths 4, 5, or 9, or reference path 43, or both, depending on implementation, so as to match the paths in the optical material, part of the two paths, lenses, fiber, and beam-splitters. For instance, the element 755 in the object path 5 has the same thickness and is made from the same material as the splitter 1. The element 755 in the reference path 43, on the other hand, has to compensate for the thickness of different materials used in the lenses in the interface optics 12, and that of the object 13, up to the layer of interest, such as the retina 17. If the fiber length of the input arms of the splitter 2 are substantially unequal, then another compensator 755 made out of silica and with a corresponding thickness has to be placed in one of the object or reference arm.

Such an arrangement and compensatory methods are known to those skilled in the art. The back-scattered light from the object path 9 is deflected by an optional total mirror 759, or it may be sent directly to the focusing element 758 and thence into the object input 28 of the output splitter 2. Bulk implementations are also possible, as described in commonly owned U.S. Pat. No. 5,975,697, in which case the polarization controller 407 and phase modulator 408 may be placed in either of the object paths 49 or 5, or in the reference path 43.

It will be understood that the photocurrents from the photodetectors 402 and 404 are differentially subtracted in the differential amplifier 45; and that the signal therefrom is then rectified or demodulated in the demodulator 406. The OCT output signal 23 is then displayed on the display device 19 under the control of computer 32.

It will be seen in FIG. 2 that the object path 4 continues with an optional mirror 759, and with focusing elements 61 and 62. After the focusing, the objected beam is denoted as 9 throughout the scanning element 10, and the interface optics 12, which may be such as a flying spot imaging instrument. Such an arrangement is, of course, particularly applicable in such as OCT and SLO procedures for the eye or OCT confocal microscopy for the skin.

It will also be noted from FIG. 2 that the input splitter 1 is a plate splitter. This avoids any reflections being sent back to the source and/or to the photodetectors. Ideally, a plate beam splitter is preferred to a cube beam splitter so as to eliminate reflections from the facets. However, another criterion for the plate of a plate beam splitter is in respect of its thickness. Even if the unused facet or surface of a plate is coated with an antireflection coating, stray light from that facet should be avoided. Even a $10^{-3}$ stray reflection is substantial for OCT, which can have a dynamic range of up to $10^{-10}$. If light is reflected from the unused facet, then ghosts in the correlation function of the core OCT system may be introduced at optical path differences which correspond to the delay between the beam reflected from the main facet and this stray reflected beam from the unused, second, facet.

Figure 3:
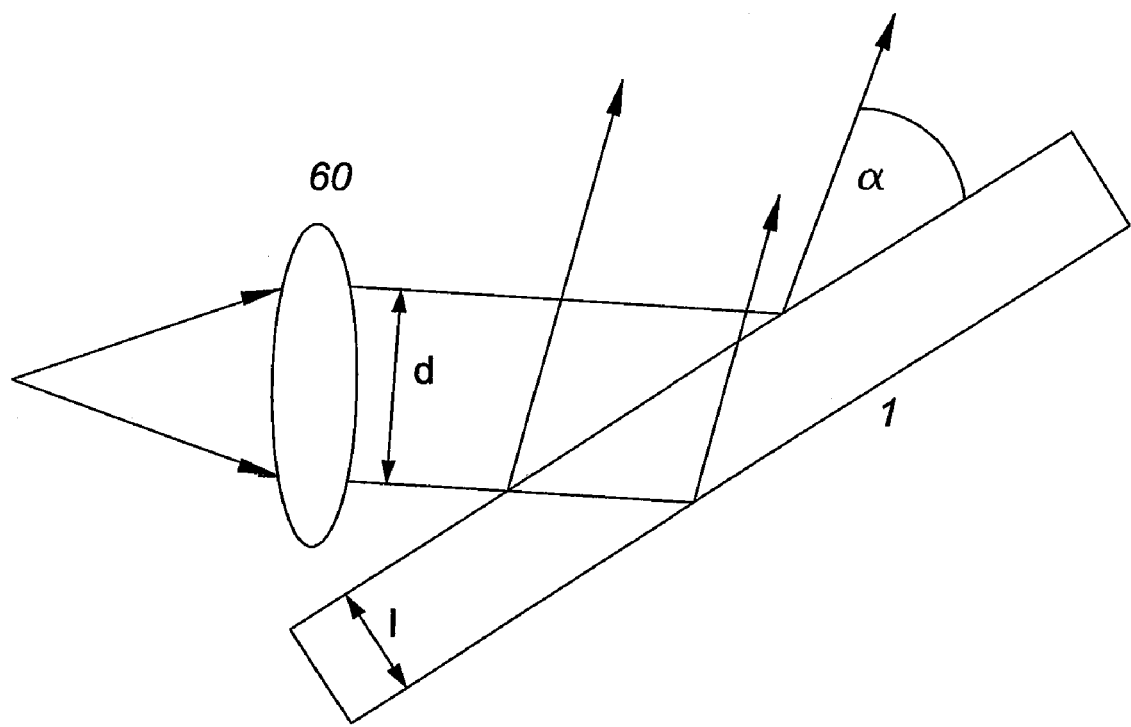
FIG. 3 shows the manner in which a beam of light traces through a plate beam splitter.

Turning now to FIG. 3, there is shown a stray reflected beam such as that which may be reflected from the unused facet of the plate in the input plate splitter 1. In order to avoid a stray beam from contributing to noise within the interferometer 40, the thickness of the plate beam splitter 1 must be larger than a minimum value for a given orientation of the angle α, as shown in FIG. 3. It can be shown that for a beam diameter d, the minimum thickness t should be $t=d/(2\cos\alpha)$. For an angle of 45 degrees, this value gives the following: $t=d/1.41$, and shows that for beam diameters of 3-5 mm, such a condition can easily be implemented by a commercially available plate beam splitter with parallel facets. Obviously, a smaller thickness is required if the facets are tilted in respect to each other, and such sloped plate beam-splitters are known in the art.

Figure 4:
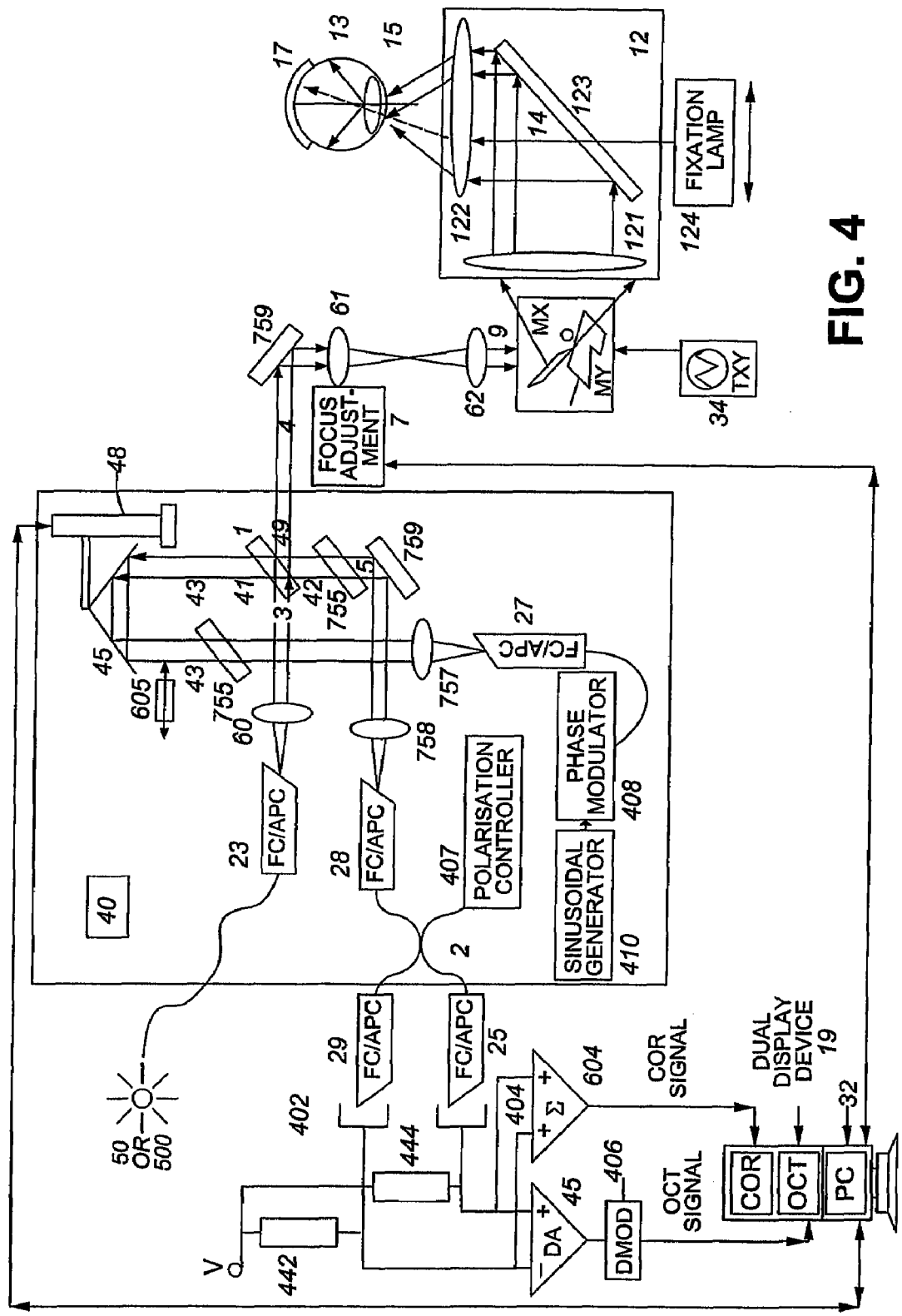
FIG. 4 shows, in diagrammatic form, a second specific embodiment of an optical mapping apparatus in keeping with present invention.

Referring now to FIG. 4, there is shown in diagrammatic form a further embodiment of an optical mapping apparatus which is in keeping with the present invention. Apparatus in keeping with that which is shown in FIG. 4 can sequentially display a confocal image for an OCT image depending on the position of the opaque screen 605. The photodetectors 402 and 404, as noted above, are of pin type or avalanche photodiode type, or photomultiplier tubes. Moreover, if the photodetectors 402 and 404 are of the avalanche photodiode type, then further functionality can be added to the configuration of optical mapping apparatus as shown in FIG. 4, in the manner much as has been described in commonly owned U.S. Pat. No. 5,975,697, particularly in FIGS. 14A and 14B.

However, the implementation of an optical mapping apparatus in keeping with present invention is such that fiber end reflection is eliminated, and easy adjustment of the optical components is allowed. Each of the reference and object beams needs only to be focused in one aperture fiber only; whereas a two bulk splitter configuration such as that described in the above noted patent requires that each beam must be simultaneously focused into two apertures.

Elimination of fiber end reflection allows good quality confocal images to be generated sequentially with the OCT images. When opaque screen 605 is removed from the light path, the large optical power which is contained in the reference beam determines a voltage drop on series resistors 442 and 444, functioning together with the avalanche photodiodes 402 and 404. This will decrease the magnitude of the inverse voltage that is applied to the avalanche photodiodes below their avalanche threshold. In such a regime, the avalanche photodiodes operate with little gain.

However, when the opaque screen 605 is introduced into the reference path 43, then only the optical signal which is returned from the target reaches the two photodetectors 402 and 404. In that case, then the avalanche photodiodes operate in avalanche mode, and the signals are added in the amplifier 604. Then, the two images can either be displayed with one channel frame grabber equipped with a switch, or they can be displayed using a dual frame grabber in the manner indicated in FIG. 4.

A similar configuration and functionality can be devised if the photodetectors are photomultiplier tubes, in which case the resistors 442 and 444 connect to suitable diodes to limit the current when the incident power is too high. In this manner, a switching regime can be implemented which is controlled by the incident power, as described above using avalanche photodiodes.

As for either regime of operation, with the opaque screen 605 either blocking or permitting beam transmission in reference path 43, two images may be displayed but only one is functional. In the OCT regime of operation, with the opaque screen 605 out, the confocal signal is too weak in comparison with the optical power, and the display for the confocal image is saturated and is therefore completely bright.

In the confocal regime with the opaque screen 605 blocking the reference path 43, the differential amplifier 45 ideally outputs a null signal, and the display for the OCT image is dark. However, due to eventual mismatch in the balance detection, some noise or a distorted confocal image may be shown, which is to be disregarded.

The summing amplifier 604 enhances the confocal optical receiver (COR) signal to be displayed by the display device 19, which as noted may be a frame grabber, a storage oscilloscope, or a suitable printer.

It has been noted that a similar configuration, at least at first blush, was shown in FIG. 14A of the commonly owned United States patent noted above; however due to fiber end reflection, the confocal channel in that configuration could only work for very reflective targets, where the reflected signal is much larger than any stray reflected signal from the fiber end. On the other hand, the embodiment of FIG. 4 shows that there will be no such signal returned from the object path other than the signal from the target. Therefore, the optical noise is much less, and an undisturbed confocal regime can be implemented.

When the apparatus of FIG. 4 operates in a confocal mode, the fiber aperture acts as a confocal restricting aperture. Depending on the fiber used, as well as on the interface optics, then a depth sectioning interval can be determined. In the case of the retina of a human eye, that depth should be in the range of 0.5-2 mm. In that case, constant depth imaging, which is termed to be generation of C-scan images, is possible by selecting the depth to be imaged using the focusing elements 60 or 61, via an axially shifting element 7 which provides focus adjustment. It should be obvious for those skilled in the art to realize that equivalently, one of the two focusing elements, 121 or 122, or both, which are part of the interface optics 12, can be moved to adjust the focus. For simplicity only, the focus adjustment block is shown in FIG. 4 tied to the lens 61; obviously the block 7 can control the position of elements 121 or 122, or both.

If focus adjustment operates in synchronism with the depth scanning in the OCT channel, then a dynamic focus arrangement is provided; this assures that when the opaque screen 605 is moved in or out, both images, confocal and OCT collect images from the same depth.

The interface optics 12 can be implemented with one or two lenses as shown in FIG. 4, or one or two mirrors, according to configurations known in the art of laser scanning of the retina. For eye guidance, a fixation lamp 124 is provided, which via a fixation splitter 123, a beam-splitter, a dichroic filter, a cold mirror or a hot mirror, sends light 14 into the eye according to means known in the art. For instance, usually the source 50 or 500 emits in infrared, 700-900 nm, therefore for low loss of the object beam 9, a hot mirror is used to allow visible light, red, yellow or green to pass to the eye. A cold mirror 123 can also be employed, in which case the object beam 9 is transmitted through 123 and the fixation beam is reflected from 123. It is however preferable for keeping the dispersion low in the object beam 9 to use the fixation splitter 123 in reflection. When the fixation splitter 123 is used in transmission by the object beam 9, then a compensation plate 755 has to be introduced in the reference beam of the interferometer.

It is also to be noted that the resultant images can be displayed in linear or logarithmic scale on a gray or false color coded format. When OCT and COR images are to be displayed separately, then a special display device 19 having dual display capabilities is required, such as a dual channel variable scan frame grabber.

It will, of course, be evident to those skilled in the art that focusing elements 60, 61, 62, 121, 122, 757, and 758, could be mirrors as well as lenses.

Figure 5:
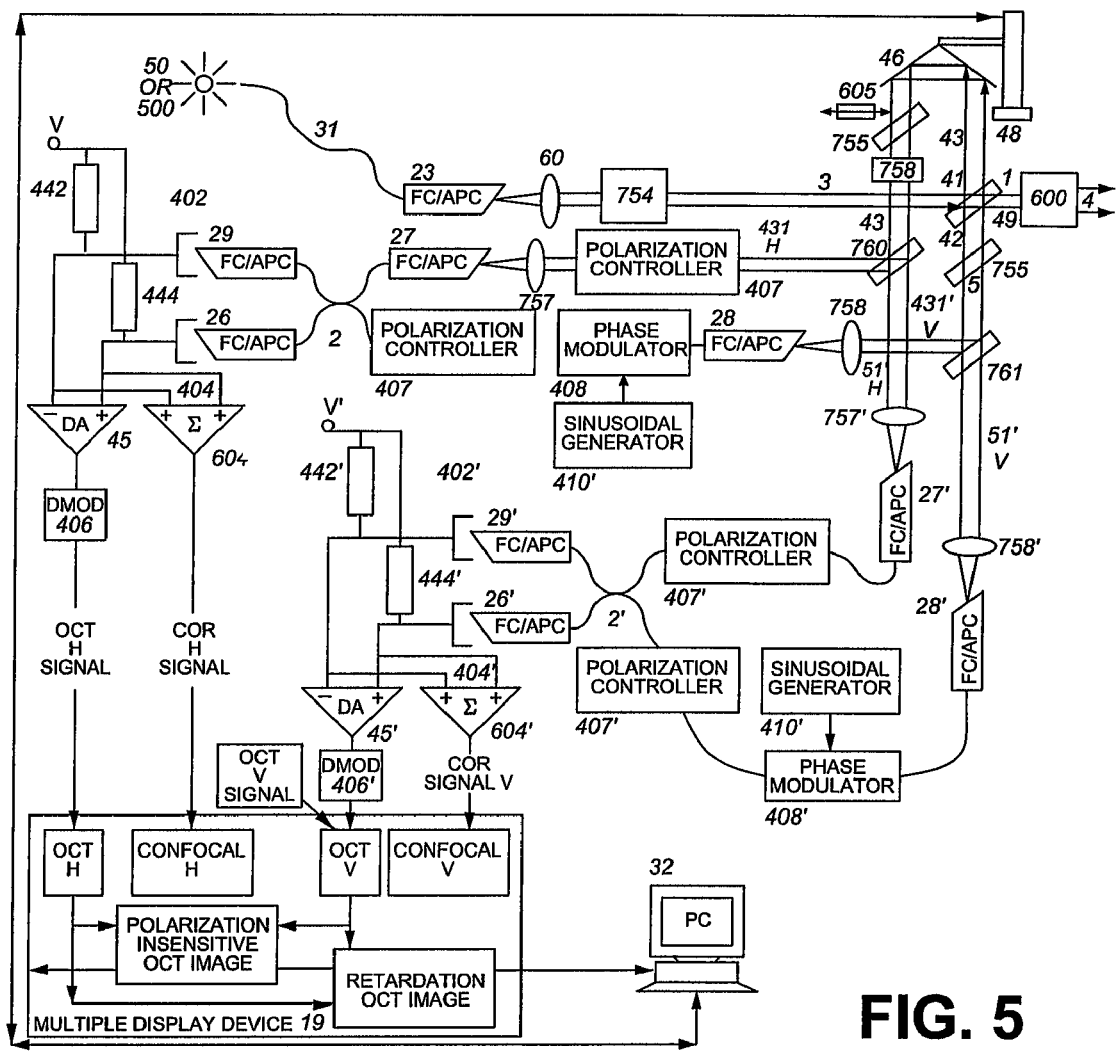
FIG. 5 shows, in diagrammatic form, yet another specific embodiment of an optical mapping apparatus in keeping with the present invention, where the system can simultaneously display two polarization sensitive OCT images with sequential display of polarization sensitive confocal images.

Referring now to FIG. 5, another embodiment of an optical mapping apparatus in keeping with the present invention is diagrammatically shown. This embodiment has a two channel polarization sensitive configuration. The embodiment of FIG. 5 differs from that of FIG. 4 in that two plate polarization splitters 760 and 761 are employed, and the light that is launched into the system is polarized linearly by the polarizer 754, either perpendicular to the page (vertically) or in the plane of the page (horizontally).

To sense the birefringence of the object, the object beam 4 is launched via a retarder 600 which, in one of the implementations, transforms the polarization state of light emerging from the beam-splitter 1 into a circular state. If the transmission of the wave through the beam-splitter 1 does not alter the linear polarization, then the retarder 600 is in the form of a quarter wave plate oriented at 45° from the plane of the page. The light backscattered from the target has an elliptical polarization due to the birefringence of the object 13, and as the light crosses the retarder 600 back into the apparatus, it will be separated into horizontal and vertical polarization components by the polarization beam splitter 761. When beam 4 encounters an ideal mirror, the beam 5 has linear polarization orientation in a direction perpendicular to that launched by the polarizer 754.

It should also be noted that there is a duplication of a number of the elements that are shown in FIG. 5, and which are constituent elements in the optical mapping apparatus which is illustrated; and all such duplicate elements are indicated with the same reference numeral but have a "prime" indicator which is shown as well. The function of operation of such elements will be therefore clearly understood.

The returned object beam 5 is split by splitter 761 into a beam 51, which has horizontal orientation of polarization, H, and beam 51' which has a vertical orientation of polarization, V.

Due to reflections at 1 and 46, the polarization of the reference beam 43 deviates from linear and is corrected in the polarization corrector rotator element 756 which also rotates the linear state to 45° from the plane of the page. When the linear state launched by 754 into the apparatus is not altered by reflections at 1 and 46, 756 is in the form of a half-wave plate with its axes rotated at 22.5° from the plane of the page. In this way, a linear polarization state at 45° to the plane of the page is generated, and consequently beams of equal amplitude but of orthogonal polarization are output from the polarization beam-splitter 760, a horizontal polarization component H, 431 and a vertical linear polarization component V, 431'.

The two horizontal components 431 and 51 are combined in the single mode splitter 2 well; and the two vertical components 431' and 51' are also combined in the single mode splitter 2' as well. Each of those splitters 2 and 2' may be either ordinary single mode couplers, or splitters that are particularly intended to maintain polarization.

The advantage of the configuration of optical mapping apparatus as shown in FIG. 5 is that such configuration may employ ordinary fiber, and is therefore capable of being produced at relatively low cost. In such circumstances, the polarization controllers 407 and 407' which are placed on the arms of the fiber couplers 27 and 28 are used to maximize the signal. Moreover, the use of the phase modulators 408 and 408' is optional.

However, in the event that the phase modulators 408 and 408' are used, it is possible to drive them at the same frequency. In that case, only one sinusoidal generator 410 is necessary, and the other sinusoidal generator 410' is redundant. This is possible because the two channels are independent.

Once the two polarization components have been separated, then different combinations of the two demodulated signals can be generated. For example, polarization insensitive images can be obtained by evaluating CI=[CONFOCALH+CONFOCALV] in the confocal channel and OCTI= $[(OCTV)^2+(OCTH)^2]^{1/2}$ in the OCT channel; and the phase retardation CONFOCAL$\phi$ of the signal can be obtained by CONFOCAL $\phi$=arctan(CONFOCALV/CONFOCALH)$^{1/2}$ in the confocal channel and by OCT$\phi$=arctan (OCTV/OCTH) in the OCT channel. Alternatively, using two logarithmic amplifiers, the phase retardation can also be obtained by CONFOCAL$\phi$=arctan {exp[0.5(log(CONFOCALV)−log (CONFOCALH))]} in the confocal channel, and by OCT$\phi$=arctan {exp[(log(OCTV)−log(OCTH)]}. Since logarithmic amplifiers are common, a simple direct calculation of the last value noted above is easily obtained.

Polarization sensitive images are useful in determining the retardation and the thickness of the retinal nerve fiber layer, the cornea of the human eye, in investigating the Purkinje reflections from the anterior chamber, and to evaluate the level of burns in the tissue, etc.

As has already been explained in connection with the embodiment shown in FIG. 4, by introducing the opaque screen 605 into the reference beam 43, both couplers 2 and 2' are deprived of the high power of the reference beam, and they will receive the object signal only via beams 51 and 51', having respect of polarization directions H and V. In this way, sequential polarization sensitive OCT imaging, with polarization sensitive confocal imaging, becomes possible, using simple single mode directional couplers. This is the equivalent with sequential display of two pairs of polarization sensitive images with different depth resolution as determined by the coherence length of the source 50 or 500 when the screen 605 is out; and by the confocal aperture of the fiber input 28 and 28' when the screen 605 is in.

Figure 6:
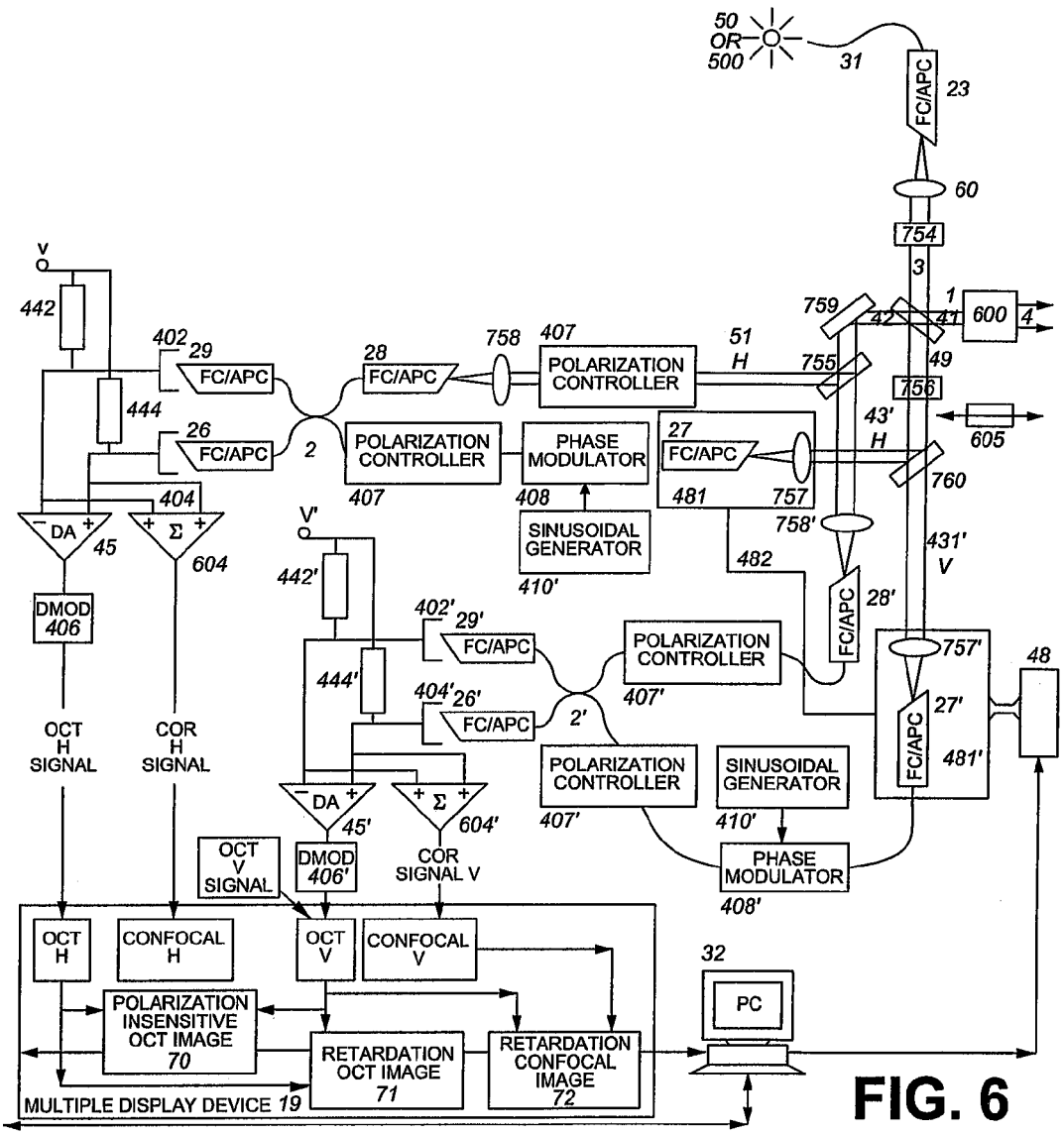
FIG. 6 shows, in diagrammatic form, a similar embodiment to that of FIG. 5, where the first splitter is used in reflection by the object beam and in transmission by the reference beam, and mirrors in the reference beam have been eliminated.

Turning now to FIG. 6, a similar embodiment to that of FIG. 5 is shown, but in this case the first splitter 1 is used in reflections by the object beam 4, and in transmission by the reference beam 43.

Using the plate beam splitter 1 in reflection by the object beam 4 has the advantage of equal glass thickness in the object beam 9 and the reference beam 3, which simplifies the dispersion compensation; so that fewer plates 755, or plates of small thickness, are required. It should be obvious that with respect to FIG. 6, the optimized percentage 1–γ refers to the percentage of light which is reflected by the plate beam splitter 1; while with respect to FIGS. 2, 4, and 5, the optimized percentage 1–γ refers to the percentage of light which is transmitted by the beam splitter 1.

A further improvement, which is also applicable to the embodiments of FIGS. 4 and 5, is that the inputs of the couplers or output beam splitters 2 and 2' can be placed on supports 481 and 481', respectively, directly on the translation stage 48. Once again, this precludes the necessity for mirrors 46. However, both of the support blocks 481 and 481' are acted upon synchronously, as shown by the line 482 connecting the two blocks. In fact, via a mirror, the beam 431 can be directed to propagate parallel to 431', and the support 481 can be placed together with support 481' on the stage 48.

Figure 7:
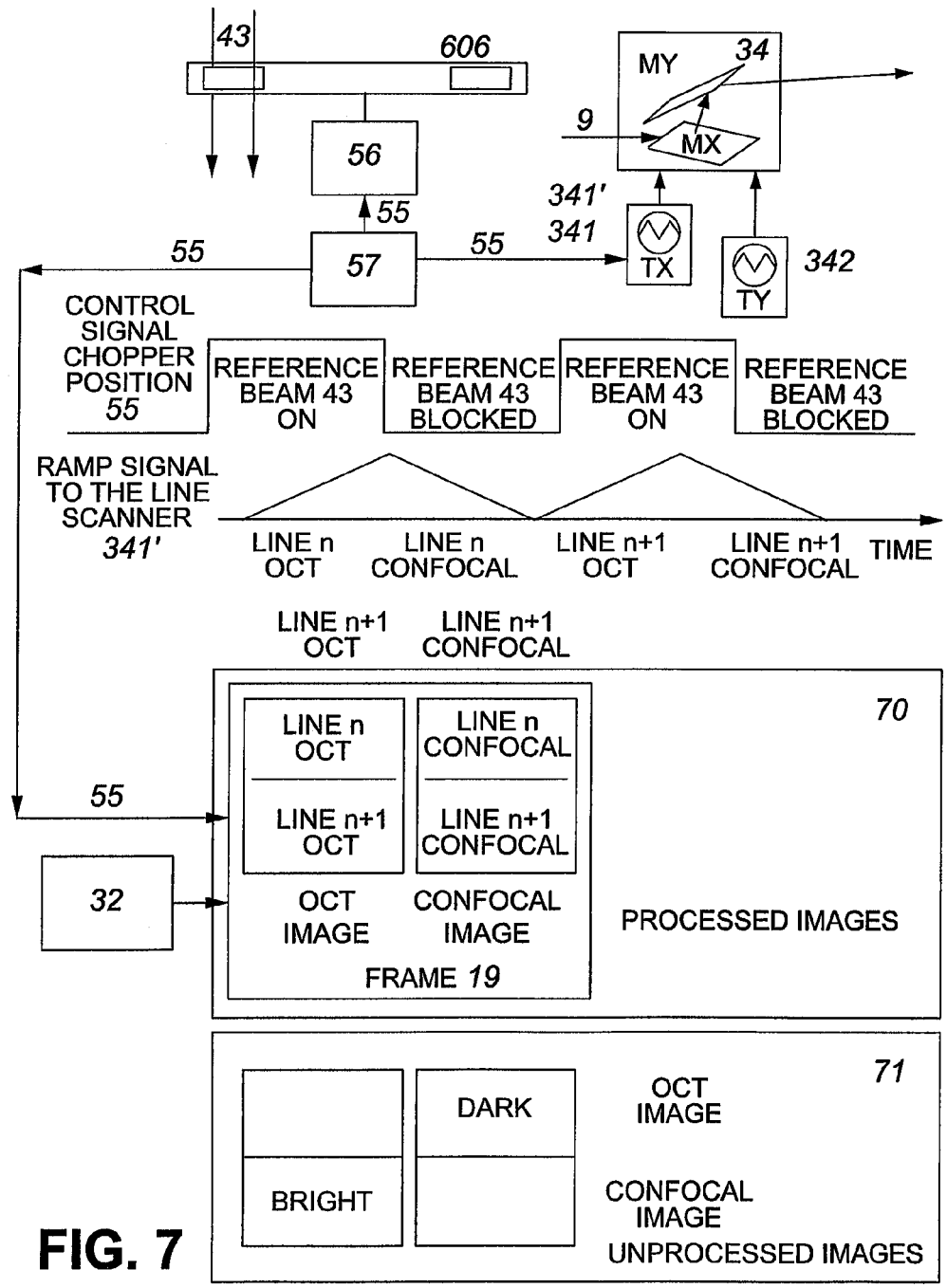
FIG. 7 shows, in diagrammatic form, a switching scheme from OCT to confocal regimes synchronous with the line scanner.

FIG. 7 shows in diagrammatic form, a scheme to switch between the OCT regime and the confocal regimes which operates fast, and is synchronous with the line scanner. The opaque screen is in the form of a chopper disk 606, whose position in and out of the reference beam 43 is synchronized by the signal 55 delivered by the electronic block 57 to the driver 56. The driver 56 may be a stepping motor whose angular rotation can be precisely controlled. As another alternative, the driver 56 may be a rotor whose rotation is sensed by the driver 56 by means known in the art, such as an LED and a photodiode placed on either side of the chopper disk, which generate the triggering signal 55 to control the display device 19 and the generator 34 of the line scanner, and thus generates the ramp 341. During the duration of one ramp, the chopper allows the beam 43 through and during the other ramp, and the beam 43 is blocked by the disk 606.

The final images produced by the display device 19 consists of two images, one OCT, formed during the time interval when the reference beam was allowed through the chopper disk 606; and the other Confocal, formed during the time interval when the reference beam was blocked by the disk 606. The two insets illustrate two possibilities. The inset 70, a case of processed images, refers to an electronic configuration where by means known in the art, the parts of the two images which are idle due to the switching process are not displayed or they are blanked out. Two arbitrary successive lives η and η+1 are shown in the raster. In the OCT channel, no image is displayed during the time interval when the reference beam is blocked, when the signal in the OCT channel is very low; and in the Confocal channel, no image is displayed during the time interval when the reference beam is on, in which case the Confocal signal is high due to the high power in the reference beam 43.

The inset 71, a case of unprocessed images, shows a simpler configuration where the device 19 displays the signal on the whole period of the signal applied to the transverse scanner. In this case, the OCT channel and the Confocal channel display useful images during one half of the whole screen. The other half of the screen is dark in the OCT image and bright in the confocal channel. The part of the screen bright in the confocal image corresponds to the useful part of the OCT image and the part of the screen dark in the OCT image corresponds to the useful part of the screen in the Confocal image.

Figure 8:
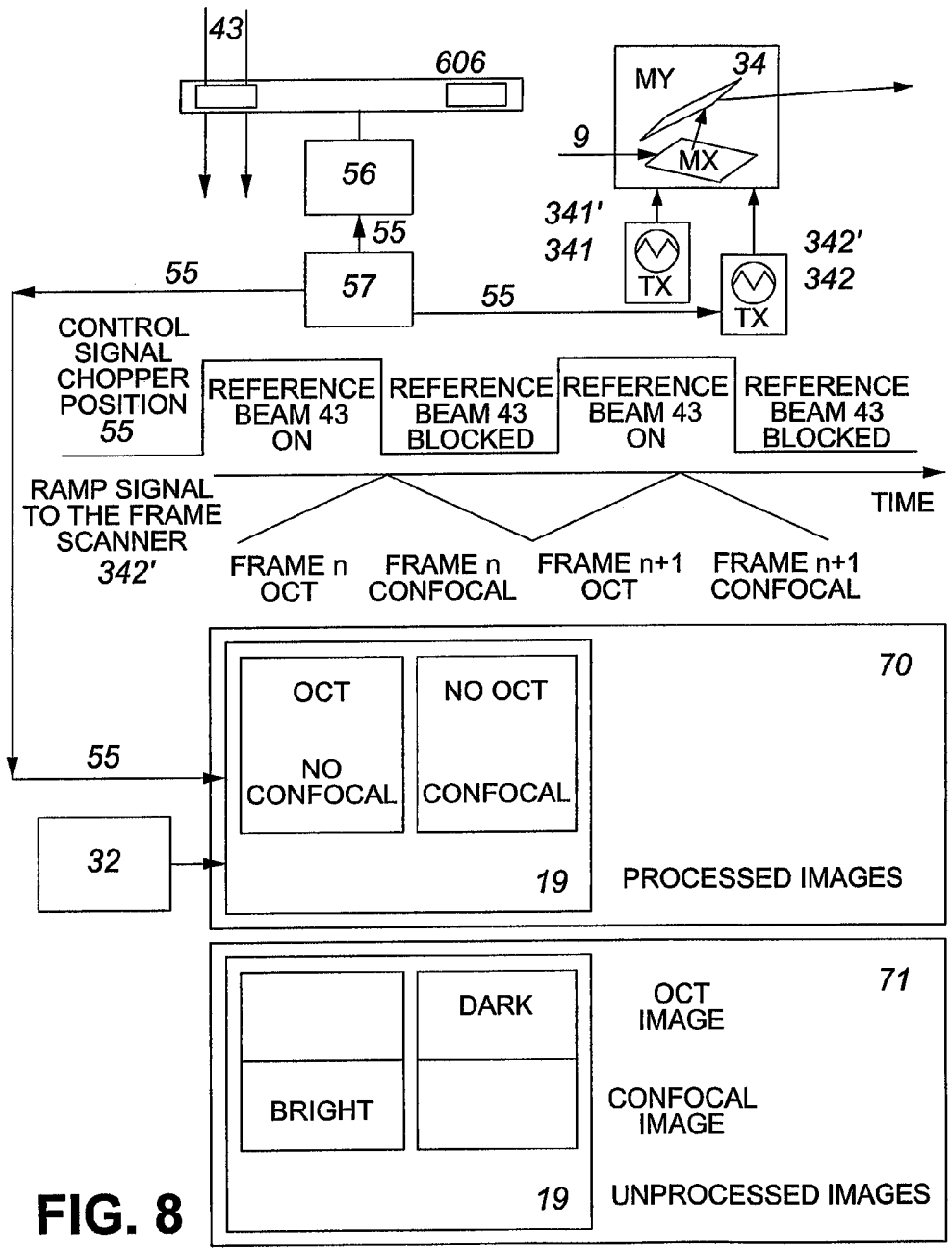
FIG. 8 shows, in diagrammatic form, a switching scheme from OCT to confocal regimes synchronous with the frame scanner.

FIG. 8 shows, in diagrammatic form, a switching scheme from the OCT regime to the confocal regime of operation which operates synchronous with the frame scanner. The configuration is similar to that shown in FIG. 7 with the difference that now the signal 55 controls the generator of the frame scanner, 342, and the switching is synchronous with its output signal, 342'. This is a case where the chopper 606 is slow, in which case the switching cannot be performed at line rate but at the lower rate of the frame. Again, two possibilities exist, 70 where the useless parts of the OCT and Confocal images are blanked out; or 71, where they are displayed, dark in the OCT channel and bright in the confocal channel.

FIGS. 7 and 8 are applicable to the embodiments described in FIGS. 2, 4, 5, and 6. When a configuration of switching as that described in FIG. 7 or 8 is used in the embodiments shown in FIGS. 5 and 6, the switching operates with pairs of images or multiple images. Therefore, OCT screen in FIGS. 7 and 8 means both OCT channels, which could be OCTH and OCTV, or a polarization insensitive image OCTI and a retardation OCT image OCTφ, or all of these four images and combinations thereof, while Confocal screen in FIGS. 7 and 8 means both confocal channels, Confocal H and Confocal V, or polarization insensitive image CI together with the confocal phase retardation CONFOCALφ, or all of these four images and combinations thereof.

It should be obvious to those skilled in the art to realize that other devices can be used instead of the chopper 606 to accomplish the same function of switching the intensity of the reference beam, such as electro-optic modulators or liquid crystals, to block or attenuate the reference beam 43 in synchronism with the line scanner for the diagram in FIG. 7 and with the frame scanner for the configuration in FIG. 8.

It should also be obvious for those skilled in the art that instead of using the pulse 55 generated by the driver 57 it is possible to drive the display device 19 with a signal proportional with the position of the transverse scanners as described in a co-pending patent application entitled "Optical Mapping Apparatus with Adjustable Depth Resolution and Multiple Functionality", by A. Gh. Podoleanu, J. A. Rogers, G. Dobre, R. Cucu, D. A. Jackson, filed in the US Patent Office, Ser. No. 10/259,671, on 30 Sep. 2002.

The sequential operation of the apparatus in the two regimes may serve different goals. For instance, the apparatus may be first switched in the confocal regime prior to OCT imaging. It is much easier to adjust the position and orientation of the object or tissue to be imaged in the confocal than in the OCT regime.

In applications such as biology, imaging with high transverse resolution is required. OCT is affected by speckle and therefore, the confocal image may offer clearer, superior detailed transverse information than the OCT. Speckle may cover fine borders of micrometer size features which may be distinguished in the confocal channel.

Successive imaging in the two regimes may offer more information than using only one channel. Details in the transverse section in the confocal image may lose sharpness in the OCT regime with the compensated advantage of better depth resolution.

One particular application is the case where polarization sensitive OCT imaging is required of birefringent object layers beneath other birefringent layers which may alter the polarization state. Such an example, consists of a birefringent plate which continues with a non-birefringent plate at similar depths beneath a sheet of stretched polyethylene, other polymer sheets which when stretched become birefringent. Accurate OCT determination of birefringence effects in the plates requires elimination of the birefringence effects due to the polyethylene-sheet. In this case, the optical mapping apparatus can operate in the following way. Confocal polarization sensitive images are collected of the non-birefringent plate beneath the sheet while actuating on the variable compensator. Values of the retardation and axis orientation are sought where the CONFOCALϕ image is uniform as possible. This corresponds to a position of the variable compensator which eliminates the birefringence effects of the intermediate sheet. Then, maintaining the adjustments of the variable compensator, the apparatus is directed towards imaging the birefringent plate. With the birefringence effects of the polyethylene removed, accurate OCTI and OCTϕ images are subsequently obtained.

This method could obviously be also applied to those biologic imaging cases where layers manifest non-birefringence properties in transverse section beneath a homogenous birefringent layer.

A specific particular case in this respect is that of imaging the retina 17 of an eye 13. Accurate OCT imaging of the retina requires compensation for the birefringence of the anterior segment. When the apparatus operates in the confocal regime of operation, the variable compensator 600 may be used to compensate for the birefringence of the anterior segment using methods known in the art, such as those disclosed in U.S. Pat. No. 6,356,036. In opposition to the goal for which such compensation is performed in that patent, where retardation of the retina is evaluated using the same polarization sensitive confocal technology as that used in the compensation process, the present application provides that such compensation is performed using the apparatus according to the invention in confocal regime prior to image the retina using the apparatus in the OCT regime. More accurate B-scan and C-scan of the retina are obtained if the OCT imaging is performed through a compensator 600 which compensates for the anterior segment birefringence.

In FIGS. 5 and 6, both OCT interferometers select signal from the same depth and the two interferometers operate on orthogonal polarization to offer polarization sensitive imaging. The diagrams in FIGS. 5 and 6 may be also employed to generate simultaneously OCT images from two different depths by introducing the following two alterations: (i) adjusting the retarder 600 to populate with equal strengths both linear polarization orientations H and V from a mirror used as a target and (ii) by introducing an optical path axially offset between the two interferometers, for instance by moving the reference input 27 and lens 757 or input 27' and lens 757' in FIG. 5 or one of the two supports 481 or 481' in FIG. 6. In this way, two OCT en-face images separated by the offset Z are generated simultaneously. If the retarder 600 is a quarter wave plate, then its axes need to be rotated by 22.5° in relation to the plane of the figure.

Similar operation could be obtained by reconfiguring the embodiments in FIGS. 5 and 6. By removing the compensator 600, polarizer elements 754 and 756 and employing non-polarizing beam-splitters 760 and 761, the two channels become substantially identical. If after these changes, the optical path difference in one interferometer is slightly changed, the apparatus according to FIG. 5 or 6 generates simultaneously OCT images from different depths.

In both implementations described above, to prevent the loss of definition, the difference Z in the optical path between the two interferometers has to be smaller than the depth range allowed by the confocal aperture, determined by the fibre aperture, lenses 758, 758' and lenses 61, 62, interface optics 12 and lens 15. In the case the object is the retina 17 of an eye 13, then the difference between the two depths Z could be up to 300 µm. When the screen 605 is introduced into the reference beam, both confocal receiver amplifiers 604 and 605' deliver the same confocal image.

Other embodiments and alternative arrangements to the OCT and optical scanning apparatus which has been described above may occur to those skilled in the art, without departing from the spirit and scope of the appended claims.

Other modifications and alterations may be used in the design and manufacture of the apparatus of the present invention without departing from the spirit and scope of the accompanying claims.

It should be noted that use of the word substantially is intended to imply that the relationship being defined is technically close to the defined quantity; but it is well understood that equality, for example, is not always practically possible.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

The invention claimed is:

1. An optical mapping apparatus comprising an OCT apparatus wherein an optical beam is transferred through interface optics to an object to be scanned and is reflected back therefrom through an OCT channel for analysis, a transverse scanning means, focusing adjustment means, analyzing means, depth adjustment means, and display means; wherein said OCT apparatus comprises a source of low coherence or adjustable coherence light, an OCT interferometer, and image display means;

said interferometer comprising an output beam splitter having object beam and a reference beam input ports, and an input beam splitter having object beam and reference beam output ports; wherein said output beam splitter combines an object beam and a reference beam at its respective object beam and reference beam inputs;

wherein said input splitter transfers $1-\gamma$ of light input to it from said light source to the respective object beam output port, and the remainder $\gamma$ of the input light by cross transmission to its respective reference beam output port so as to derive a splitting ratio $\epsilon=(1-\gamma)/\gamma$;

wherein the light from the reference beam output port of said input splitter is directed to the reference beam input port of said output beam splitter; and wherein light reflected and scattered back from said object is output from the object beam output port of said input splitter and is reinjected into the object beam output port of said input splitter and is cross transmitted to said object beam input port of said output splitter;

wherein said input beam splitter is a bulk beam splitter, and said output beam splitter is a single mode fiber coupler equipped with fiber ends that are cleaved at an angle at all inputs and outputs thereof;

wherein said transverse scanning means comprises a line scanner and a frame scanner, whereby transverse scanning of an object is effected by an optical image beam that is output from said input beam splitter and is directed over a predetermined target position on said object;

wherein said interface optics functions to transfer said optical imaging beam from said transverse scanning means to said object, and functions to transfer an optical output beam which is reflected and scattered back from said object to said input beam splitter through said transverse scanning means;

wherein said focusing adjustment means is placed either between said input splitter and said transverse scanning means, or between said scanning means and said object to be scanned, so as to focus said optical imaging beam at a specific depth within said object;

wherein said depth adjustment means functions to alter an optical path difference within said interferometer over a predetermined amount for at least one point in said transverse scanning means; and wherein said display means is adapted to generate and display at least an OCT image derived from said combined object and reference beams.

2. The optical mapping apparatus of claim 1, wherein said transverse scanning means is settable to electively direct said optical imaging beam over a respective line or area of said object by respective operation of said line scanner or said frame scanner.

3. The optical mapping apparatus of claim 1, and further comprising modulation means to introduce signal modulation chosen from the group consisting of intensity modulation, phase modulation, and combinations thereof, in said interferometer.

4. The optical mapping apparatus of claim 3, wherein said interferometer has air signal paths and fiber signal paths, and wherein said modulation means is adapted to introduce signal modulation in the group of paths consisting of said air signal paths, said fiber signal paths, and combinations thereof.

5. The optical mapping apparatus of claim 1, wherein said depth adjustment means functions to alter said optical path difference in steps.

6. The optical mapping apparatus of claim 1, wherein said depth adjustment means functions to alter said optical path difference continuously.

7. The optical mapping apparatus of claim 1, wherein said output beam splitter is terminated with first and second photodetectors to implement balance detection, and an optical confocal receiver configured to create a confocal image from an output of said first and second photodetectors.

8. The optical mapping apparatus of claim 7 wherein the respective images from said interferometer and said optical confocal receiver are simultaneously displayed, and are synchronized with said transverse scanning means; whereby display of a line in an image corresponds to movement of said line scanner, and advance of a line to completion of a predetermined area on said object which is being scanned corresponds to movement of said frame scanner.

9. The optical mapping apparatus of claim 7, wherein a confocal signal channel is established in said apparatus, and wherein said object has a depth axis, said apparatus further comprising second timing means; whereby when said reference beam is blocked, said second timing means controls said mapping apparatus so as to acquire transverse images at a constant depth in said confocal channel, where the depth of the images to be acquired is selected by adjustment of said focusing adjustment means.

10. The optical mapping apparatus of claim 9, wherein an OCT signal channel and a confocal signal channel are established in said apparatus; and wherein when said first timing means controls an en-face mode, said mapping apparatus acquires transverse images in a channel chosen from the group consisting of said OCT signal channel, said confocal signal channel, and combinations thereof.

11. The optical mapping apparatus of claim 7, wherein a confocal signal channel is established in said apparatus, and wherein said object has a depth axis, said apparatus further comprising second timing means; whereby when said reference beam is blocked, said second timing means controls said mapping apparatus so as to acquire longitudinal images in said confocal channel, where the depth of the images to be acquired is selected by adjustment of said focusing adjustment means.

12. The optical mapping apparatus of claim 7, wherein an OCT signal channel and a confocal signal channel are established in said apparatus; and wherein when said first timing means controls an en-face mode, said mapping apparatus acquires transverse images in a channel chosen from the group consisting of said OCT signal channel, said confocal signal channel, and combinations thereof.

13. The optical mapping apparatus of claim 7, wherein said depth adjustment means in said interferometer and said focusing adjustment means are simultaneously controlled so as to ensure that the image generated by said OCT interferometer and by said confocal receiver are selected from the same depth, and so that the signal strength in said OCT channel is at a maximum; and wherein constant depth scans from the same depth are acquired in both of said OCT channel and a confocal signal channel which is established in said apparatus.

14. The optical mapping apparatus of claim 7, wherein said blocking means are implemented by using a chopper or an optical modulator, operated in synchronism with said scanner so as to generate a line in a final raster in such a way that the time interval of blocking the beam starts and stops in antiphase with the time interval of allowing the beam through, and such that starts and stops are synchronized with the moment when the line scanner changes the direction of movement; and wherein each frame consists of two images, one OCT and the other confocal, where half of the line in each raster bears useful image information while the other half is disregarded or discarded, and each useful half of the lines in the image produced by the OCT channel corresponds to scanning the beam transversally from one extreme to the other in one direction while the useful half of the lines in the confocal image is created during such movement in the opposite direction.

15. The optical mapping apparatus of claim 14 where said OCT image comprises at least two OCT images, and said confocal image comprises at least two confocal images provided by polarization sensitive channels and combinations thereof.

16. The optical mapping apparatus of claim 7, wherein said blocking means are implemented by using a chopper or an optical modulator, operated in synchronism with said scanner so as to generate a frame in a final raster in such a way that the time interval of blocking the beam starts and stops in antiphase with the time interval of allowing the beam through, and such that starts and stops are synchronized with the moment when the frame scanner changes the direction of movement and during each frame, only one alternate OCT or confocal image is useful, while the subsequent frame in the respective OCT channel or confocal channel is disregarded or discarded; and wherein each useful frame produced by the OCT channel corresponds to scanning the beam transversally from one extreme to the other in one direction while the useful frame produced by the confocal channel is created during such movement in the opposite direction.

17. The optical mapping apparatus of claim 16 where said OCT image comprises at least two OCT images, and said confocal image comprises at least two confocal images provided by polarization sensitive channels and combinations thereof.

18. The optical mapping apparatus of claim 7 where the information collected in a confocal imaging regime is used for one of the purposes comprising the group consisting of: to guide the imaging in a successive or quasi-simultaneous OCT regime of operation, for the adjustment of the object to be scanned prior to OCT imaging, and for identification of borders below a speckle threshold in the OCT image.

19. The optical mapping apparatus of claim 7, further comprising blocking means for blocking the reference beam.

20. The optical mapping apparatus of claim 1, wherein said object has a depth axis, and said apparatus further comprises a first timing means whereby en-face imaging of said object and longitudinal imaging of said object may be electively controlled;

wherein when said mapping apparatus operates in an en-face imaging mode, said apparatus acquires transverse images of said object at a constant depth; and wherein when said mapping apparatus operates in a longitudinal imaging mode, said apparatus acquires longitudinal images of said object in a direction parallel to said depth axis.

21. The optical mapping apparatus of claim 1, wherein said bulk beam splitter is a plate beam splitter having a pair of parallel opposed surfaces; wherein the thickness of the plate is larger than the beam diameter divided by twice the value of the cosine of the angle between the beam and the orientation of said parallel opposed surfaces; and wherein one of said parallel opposed surfaces optionally has an antireflection coating thereon.

22. The optical mapping apparatus of claim 1, wherein the outputs of said single mode fiber coupler are chosen from the group consisting of bare fibers cleaved at an angle, angled FC/APC connectors, angled ST/APC connectors, and combinations thereof.

23. The optical mapping apparatus of claim 1, wherein said light source has pigtailed connectors, and each pigtail is terminated with a polished connector which can be screwed into a corresponding female receptacle, whereby light radiation from said light source may be fed to said input beam splitter.

24. The optical mapping apparatus of claim 1, wherein said input splitter is a bulk beam splitter in the form of a plate, and the plate thereof has two opposed surfaces and sufficient thickness therebetween to laterally shift the two beams which are reflected by said two opposed surfaces so as to permit the beam reflected by one of said two opposed surfaces to be directed out a respective output port thereof, while the beam from the other of the two opposed surfaces is ignored; and wherein one of the said two opposed surfaces optionally has an antireflection coating thereon.

25. The OCT apparatus of claim 24, wherein said two opposed surfaces of said plate are parallel one to the other.

26. The OCT apparatus of claim 24, wherein said two opposed surfaces of said plate are tilted one with respect to the other so as to diverge away from one another.

27. The optical mapping apparatus of claim 1, further comprising a confocal receiver for creating a confocal image, and wherein said display means is configured to display said confocal image in conjunction with said OCT image on said display means.

28. The optical mapping apparatus of claim 27, wherein said output beam splitter is terminated with first and second photodetectors receiving said combined object beam and said reference beam, and a balance receiver is provided to generate the OCT image from signals provided by the first and second photodetectors.

29. The optical mapping apparatus of claim 28, further comprising a summator for generating said confocal image from the outputs of said second first and second photodetectors.

30. The optical mapping apparatus of claim 27, wherein the depth adjustment means and the focusing adjustment means are simultaneously controllable to ensure that the image generated by the OCT interferometer and confocal receiver are taken at the same depth.

* * * * *